United States Patent
Moss et al.

(10) Patent No.: US 11,840,592 B2
(45) Date of Patent: Dec. 12, 2023

(54) PREPARATIONS OF META-IODOBENZYLGUANIDINE AND PRECURSORS THEREOF

(71) Applicant: Molecular Insight Pharmaceuticals, Inc., New York, NY (US)

(72) Inventors: Jason Moss, New York, NY (US); Machinani Rao, New York, NY (US)

(73) Assignee: Molecular Insight Pharmaceuticals, Inc., New York, NY (US)

( * ) Notice: Subject to any disclaimer, the term of this patent is extended or adjusted under 35 U.S.C. 154(b) by 0 days.

(21) Appl. No.: 17/671,128

(22) Filed: Feb. 14, 2022

(65) Prior Publication Data

US 2023/0008878 A1    Jan. 12, 2023

Related U.S. Application Data

(62) Division of application No. 16/437,061, filed on Jun. 11, 2019, now Pat. No. 11,279,784, which is a division of application No. 14/921,898, filed on Oct. 23, 2015, now abandoned.

(60) Provisional application No. 62/069,029, filed on Oct. 27, 2014, provisional application No. 62/068,598, filed on Oct. 24, 2014.

(51) Int. Cl.
| | | |
|---|---|---|
| *C08F 230/04* | (2006.01) | |
| *A61K 51/04* | (2006.01) | |
| *C07C 279/06* | (2006.01) | |
| *A61P 35/00* | (2006.01) | |
| *C07C 277/08* | (2006.01) | |
| *A61K 31/155* | (2006.01) | |

(52) U.S. Cl.
CPC ........ *C08F 230/04* (2013.01); *A61K 51/0406* (2013.01); *C07C 279/06* (2013.01); *A61K 31/155* (2013.01); *A61P 35/00* (2018.01); *C07C 277/08* (2013.01)

(58) Field of Classification Search
CPC ............. C08F 230/04; A61K 51/0406; A61K 31/155; C07C 279/06; C07C 277/08
See application file for complete search history.

(56) References Cited

U.S. PATENT DOCUMENTS

| | | | |
|---|---|---|---|
| 4,591,630 A | 5/1986 | Gertzman et al. | |
| 5,565,185 A | 10/1996 | Hunter et al. | |
| 6,461,585 B1 | 10/2002 | Hunter et al. | |
| 7,658,910 B2 | 2/2010 | Hunter et al. | |
| 8,188,296 B2 | 5/2012 | Janssen et al. | |
| 2003/0012730 A1 | 1/2003 | Hunter et al. | |
| 2016/0115267 A1 | 4/2016 | Moss et al. | |
| 2019/0367653 A1 | 12/2019 | Moss et al. | |

FOREIGN PATENT DOCUMENTS

| | | |
|---|---|---|
| EP | 0693467 A1 | 1/1996 |
| WO | 2004035744 A2 | 4/2004 |
| WO | 2011143360 A2 | 11/2011 |
| WO | 2016065322 A1 | 4/2016 |

OTHER PUBLICATIONS

International Search Report for PCT/US2015/057222, 5 pages (dated Mar. 16, 2016).
Written Opinion for PCT/US2015/057222, 9 pages (dated Mar. 16, 2016).
Chretien, J-M. et al., "New Trends in the Synthesis of Solid-Supported Organotin Reagents and Interest of their Use in Organic Synthesis in a Concept of Green Chemistry", Tin Chemistry Fundamentals, Frontiers, and Applications, Ch. 5.5, John Wiley & Sons, Ltd.607-621.
Culbert, P. et al., "Polymer-supported radiopharmaceuticals: <123>I- and <131>I-labelled N-isopropyl-4-iodoamphetamine", Reactive Polymers, 19(3), DOI: 10.1016/0923-1137(93)90082-Q, Jun. 1, 1993, 247-253.
Hernan, A. G. et al., "New and efficient synthesis of solid-supported organotin reagents and their use in organic synthesis", J. Org. Chem., 691(8), doi:10.1016/j.jorganchem.2005.11.031, 2006, 1466-1475.
Paulekuhn, G. S. et al., "Trends in Active Pharmaceutical Ingredient Salt Selection based on Analysis of the Orange Book Database", J. Med. Chem., 50, 2007, 6665-6672.
Vaidyanathan, G. et al., "A kit method for the high level synthesis of [211 At] MABG", Bioorg. & Med. Chem., 15, 2007, 3430-3436.
Vaidyanathan, G. "No-carrier-added synthesis of meta-[131]iodobenzylguanidine", Appl. Radiol. Isot., 44(3), Jan. 1, 1993, 621-628.
Wafelman, A. R. et al., "Synthesis, radiolabelling and stability of radioiodinated m-iodobenzylguanidine, a review", Appl. Radiol. Isot., 45(10), DOI: 10.1016/0969-8043(94)90168-6, Oct. 1994, 997-1007.

*Primary Examiner* — James W Rogers
(74) *Attorney, Agent, or Firm* — ELMORE PATENT LAW GROUP, P.C.; Edgar W. Harlan; Carolyn S. Elmore

(57) ABSTRACT

The present disclosure provides purified forms of iobenguane and preparations of a precursor to iobenguane, such as a polymer, the polymer comprising a monomer of formula (I)

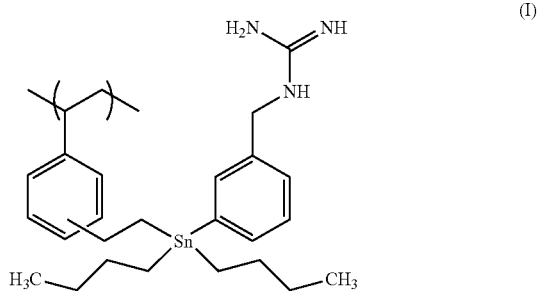

or a pharmaceutically acceptable salt thereof, the preparation comprising leachable tin at a level of 0 ppm to 850 ppm.

17 Claims, 2 Drawing Sheets

PREPARATIONS OF META-IODOBENZYLGUANIDINE AND PRECURSORS THEREOF

PRIORITY CLAIM

This application is a divisional of U.S. patent application Ser. No. 16/437,061, filed Jun. 11, 2019, which is a divisional of U.S. patent application Ser. No. 14/921,898, filed Oct. 23, 2015 (Abandoned), which claims priority to U.S. Provisional Patent Application No. 62/069,029, filed Oct. 27, 2014, and U.S. Provisional Patent Application No. 62/068,598, filed Oct. 24, 2014. The entire content of these priority applications are incorporated herein by reference.

BACKGROUND

Certain radiolabelled haloaromatic compounds have proven to be useful in nuclear medicine.

SUMMARY

Applicants have discovered that a stannylated polymer, comprising monomer of formula (I), below, if prepared according to available methods (e.g., as described in U.S. Pat. No. 7,658,910 to Duncan Hunter and Xizhen Zhu of the University of Western Ontario; hereinafter the "University Patent"), is generally contaminated with substantial levels (e.g., >150 ppm to >1,000 ppm) of leachable tin-containing by-products. See Examples 7-9 herein.

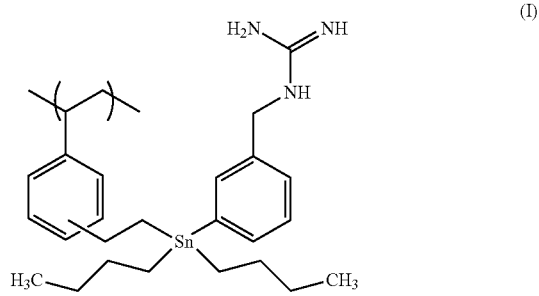

(I)

Upon treatment with iodide, such as radioisotopic iodide, the contaminated polymer comprising monomer of formula (I), prepared according to methods of the University Patent, can yield a radiolabeled iobenguane, also known as meta-iodobenzylguanidine or MIBG, with unacceptable levels of leachable tin-containing by-products.

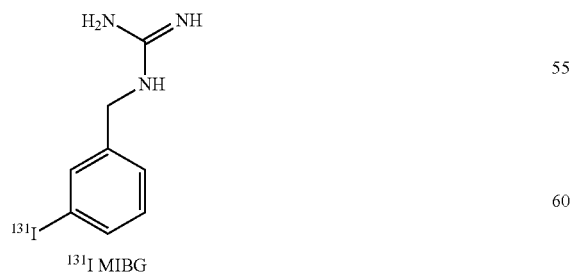

$^{131}$I MIBG

Applicants have recognized this problem and, without being bound by theory, have identified certain sources of the problem. The present disclosure describes useful solutions that address such sources, thereby providing new and desirable compositions and technologies for the preparation and use of stannylated polymers and/or radiolabeled haloaromatics such as MIBG.

For example, as described herein, Applicants have developed improved methods of preparing the polymer comprising monomer of formula (I), relative to the methods described in the University Patent, that minimize starting levels of leachable tin-containing by-products in the polymer comprising monomer of formula (I).

Also, Applicants have developed improved methods of purifying the polymer comprising monomer of formula (I), relative to the methods described in the University Patent, that minimize levels of leachable tin-containing by-products in the purified polymer comprising monomer of formula (I).

Additionally, Applicants discovered that the polymer comprising monomer of formula (I) is surprisingly sensitive to moisture, $O_2$ and/or ambient and elevated temperature. In fact, Applicants have found that the polymer gradually and continuously degrades in the presence of moisture, $O_2$ and/or at ambient and elevated temperatures, thus generating increasing levels of leachable tin-containing fragments. See Example 8 herein.

As described herein, Applicants have developed various improved technologies including, for example, methods of storing the polymer comprising monomer of formula (I) under inert gas, such as nitrogen, optionally at reduced temperature (e.g., −20° C.), that minimize the formation and/or presence of leachable tin-containing by-products in the purified polymer comprising monomer of formula (I).

Accordingly, in some aspects, provided are preparations of a polymer, the polymer comprising a monomer of formula (I):

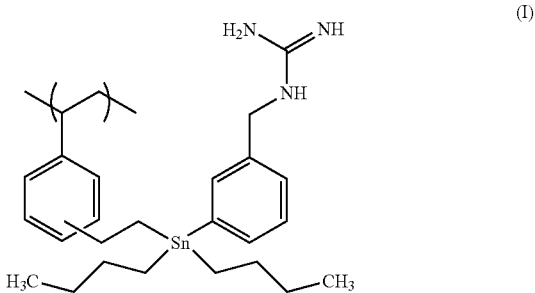

(I)

or a pharmaceutically acceptable salt thereof, wherein leachable tin is present in the preparation at a level within a range of about 0 ppm to about 150 ppm.

In some aspects, the present disclosure provides kits comprising the disclosed preparation of the polymer comprising monomer of formula (I).

In some aspects, the present disclosure provides pharmaceutical compositions comprising MIBG, or a pharmaceutically acceptable salt thereof, wherein the MIBG is formed by contacting iodine or an iodide salt with a disclosed preparation of the polymer comprising monomer of formula (I).

In some aspects, the present disclosure provides methods for providing or preparing purified polymer compositions.

In some aspects, provided is a method for preparing meta-iodobenzylguanidine (MIBG), or a pharmaceutically acceptable salt thereof, comprising contacting an iodide salt with disclosed polymer preparation as described herein.

The present disclosure provides, among other things, various technologies for manufacturing, purification, storage and/or analysis of preparations comprising polymers as described herein.

In some embodiments, the present disclosure provides polymer preparations, and technologies for providing them, that reproducibly show one or more desirable attributes (e.g., reduced level of one or more contaminants or undesirable structures) as compared with preparations that can result from prior methodologies such as those set forth in the University Patent.

In some embodiments, the present disclosure identifies a source of a problem with one or more aspects of prior technologies for synthesis, purification, and/or storage for relevant polymer preparations and/or radiolabeled haloaromatics.

In some embodiments, the present disclosure provides improvements to reaction steps and/or purification and storage protocols used in one or more prior synthesis methodologies used to make, purify and/or store preparations of a polymer comprising the monomer of formula (I).

In some aspects, provided is a method, the method comprising administering to a subject a pharmaceutical composition comprising:

(a) meta-iodobenzylguanidine (MIBG):

or a pharmaceutically acceptable salt thereof, wherein MIBG is formed by contacting an iodide salt with a preparation of a polymer comprising monomer of formula (I):

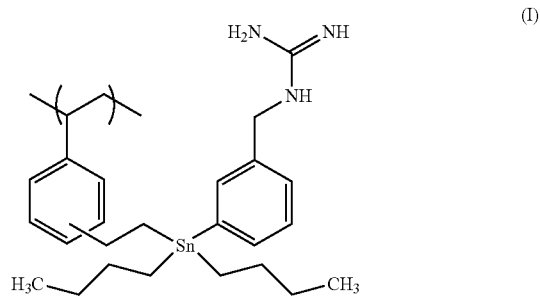

or a pharmaceutically acceptable salt thereof, the preparation of the polymer comprising monomer of formula (I) comprising leachable tin at a level of 0 ppm to 150 ppm;

(b) a pharmaceutically acceptable carrier, adjuvant, or vehicle.

In some embodiments of the method, the pharmaceutical composition comprises leachable tin at a level of 0 ppm to 150 ppm upon administration.

Figure 1:
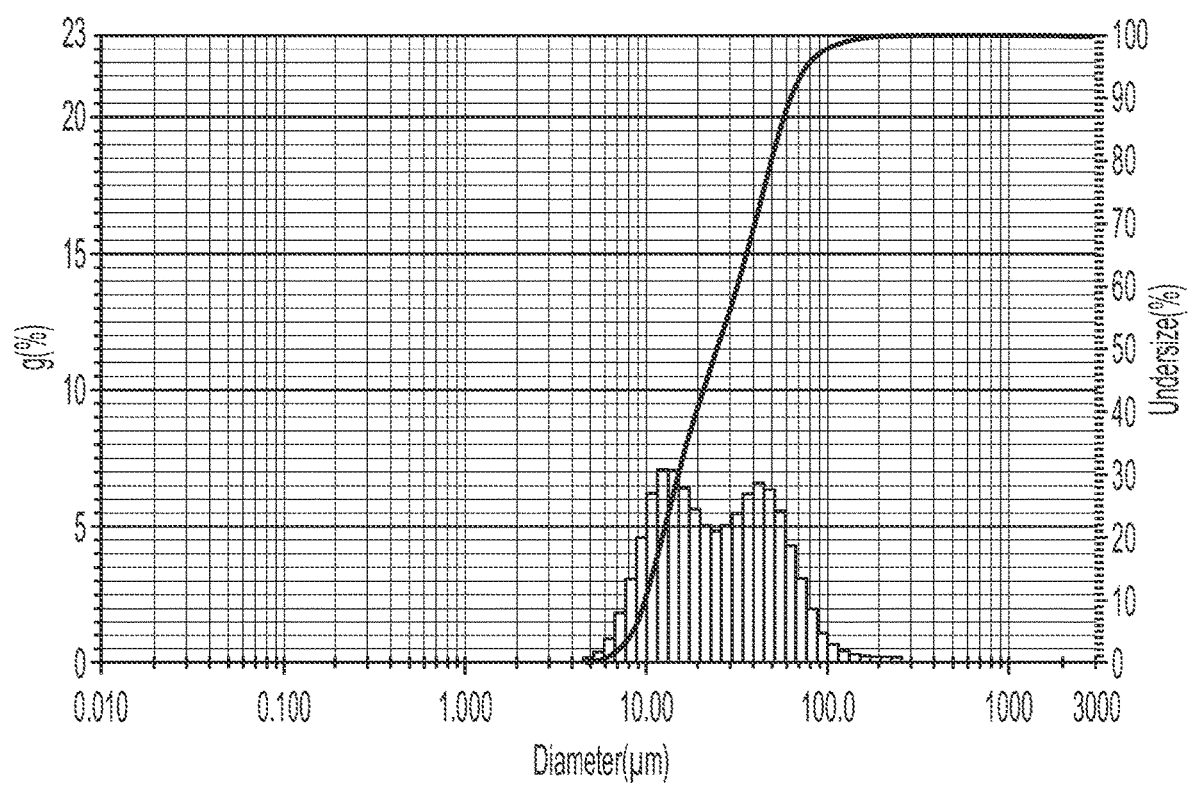
FIG. 1 illustrates typical bimodal particle size distributions for polymer comprising monomer of formula (I) made according to methods described in U.S. Pat. No. 7,658,910. Particle sizes were determined from known wet dispersion laser diffraction methods. The mean size for the bimodal particle size distribution was found to be 32.64 µm.
Figure 2:
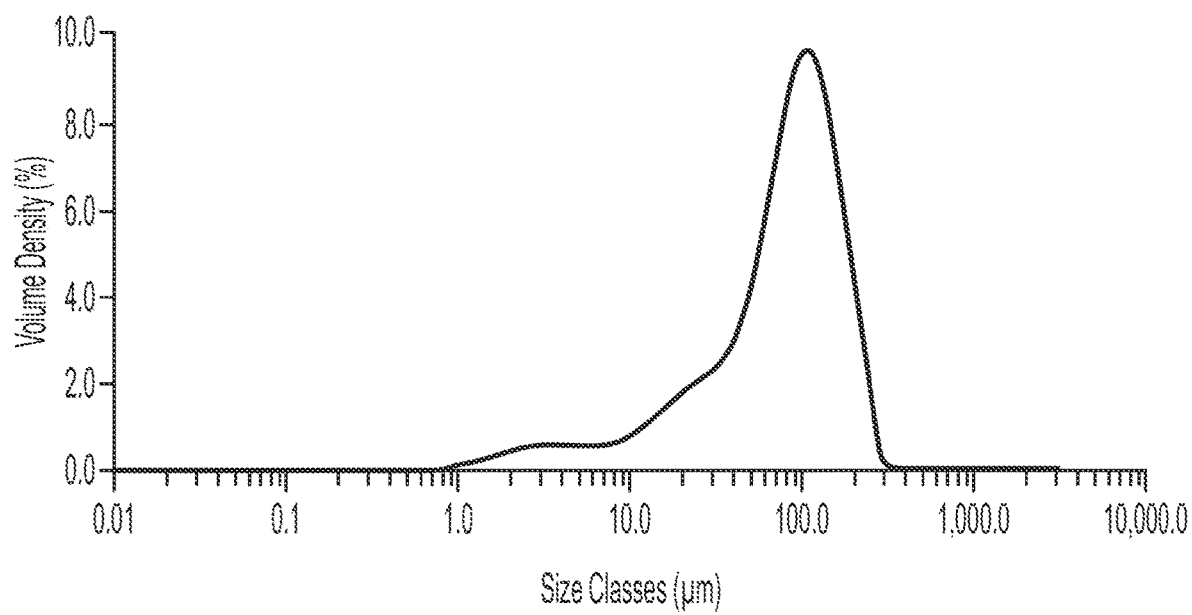
FIG. 2 illustrates typical particle size distributions for polymer comprising monomer of formula (I) made according to methods described herein such as those of Examples 1-6. Particle sizes were determined from known wet dispersion laser diffraction methods. Mean test results of Dv10, Dv50 and Dv90 are presented in the table below.

| Replicate | Dv10 (µm) | Dv50 (µm) | Dv90 (µm) | Volume Mean Diameter (VMD) (µm) | Weighted Residual (%) | Obscuration (%) |
|---|---|---|---|---|---|---|
| 1 | 15.350 | 86.736 | 174.910 | 91.930 | 0.33 | 11.14 |
| 2 | 18.830 | 78.235 | 154.065 | 83.541 | 0.29 | 11.47 |
| 3 | 16.861 | 88.760 | 183.930 | 123.024 | 0.38 | 11.58 |
| Mean | 17.0 | 84.6 | 171.0 | 99.5 | N/A | N/A |
| % RSD | 10.3% | 6.6% | 9.0% | N/A | N/A | N/A |

DETAILED DESCRIPTION OF CERTAIN EMBODIMENTS

Radiolabeled Haloaromatics

Certain radiolabelled haloaromatic compounds have proven to be useful in nuclear medicine. For example, MIBG, can be radiolabeled with iodine for use as a diagnostic or therapeutic agent. In particular, radiolabeled MIBG is used in a scintigraphy method called an MIBG scan. Different iodine radioisotopes are used to label MIBG for different applications. For example, iodine-123 (e.g., AdreView® iobenguane I-123) is typically used for imaging purposes (e.g., for cardiac or tumor imaging); iodine-131 (e.g., Azedra® iobenguane I-131), which is longer lived and provides much higher radiation intensity, is generally used for therapeutic applications (e.g., where tissue destruction is desired, such as in the treatment of tumors), but can also be used as an imaging agent. Iobenguane localizes to adrenergic tissue and thus can be used, for example, to target tumors such as pheochromocytomas, paragangliomas, neuroblastomas, and/or other neuroendocrine tumors.

It is desirable to produce isotopically-labeled MIBG in high yield relative to cold non-radioactive MIBG. Among other things, it is appreciated that, upon treatment of a patient with an infusion of MIBG, the presence of cold non-radioactive "carrier" MIBG molecules may inhibit uptake of radiolabeled MIBG, resulting, for example, in less tumor radiation and/or increased risk of cardiovascular side effects. The administration of high concentrations of radiolabeled MIBG relative to cold MIBG thus provides at least two significant benefits: greater tumor uptake and reduced pharmacological toxicity such as, for example, reduced frequency or severity of side effects, such as hypertension, nausea or vomiting, which can often occur during MIBG infusion.

Efforts to produce isotopically-labeled iobenguane in high yield have led to the use of organotin precursors that are sufficiently reactive to undergo facile exchange with radioiodide. For example, U.S. Pat. No. 5,565,185 discloses a process for radiolabelling MIBG by iododestannylation of a small-molecule trialkylaryltin precursors of formula (II), shown below in Scheme 1. However, this process is impractical because tin-containing by-products are formed that leach into solution with the radiolabelled MIBG. These toxic tin-containing contaminants are difficult to separate from the radiolabelled MIBG.

Leachable organotin compounds are highly toxic. Tributyltin-containing compounds (e.g., tributyl tin hydride or tributyl oxide) were once widely used as marine antibiofouling agents to improve the efficiency of ocean-going ships, but concerns over the toxicity of these compounds led to a worldwide ban by the International Maritime Organization. Some reports describe negative biological effects on marine life at concentrations as low as 1 nanogram per liter. See Gajda, M. and Jancso, A. (2010) "Organotins, formation, use, speciation and toxicology" *Metal Ions in Life Sciences* vol. 7, pp. 111-152 (Eds. A. Sigel, H. Sigel, R. K. O. Sigel), RSC Publishing Thomas Graham Hause.

U.S. Pat. No. 7,658,910 describes a solution to this problem, particularly a stannylated polymer comprising monomer of formula (I), shown above, and a process for radiolabelling MIBG by iododestannylation of MIBG from the polymer comprising monomer (I). In principle, iododestannylation of the polymeric precursor comprising monomer (I) sheds radiolabeled MIBG into solution, whereas the toxic tin-containing by-products remain bound to the insoluble polymer. The present disclosure encompasses the insight that, in practice, leachable tin-containing side products are co-produced with the polymer, and can remain at undesirable levels in preparations of radiolabeled MIBG. The present invention provides the insight that there is a need for improved preparations of the stannylated polymer comprising monomer of formula (I), and the MIBG therapeutic (e.g., radiolabeled MIBG, and particularly MIBG labeled with radioactive iodine such as I-123 or, in particular embodiments, I-131), that are substantially contaminant free.

Polymer Preparations

As discussed, Applicants discovered that preparations of polymers comprising monomer of formula (I) manufactured according to prior technologies including, for example, those described in the University Patent, are generally contaminated with unacceptable levels of leachable tin and, furthermore, that such levels typically increase with time. As described herein, Applicants have modified certain of the reactions described in the University Patent, and furthermore have developed purification protocols and storage conditions that effectively reduce the levels of leachable tin in preparations of polymers comprising monomers of formula (I), and effectively reduce the levels of leachable tin in the resulting MIBG therapeutic and pharmaceutical compositions comprising the same.

Scheme 1

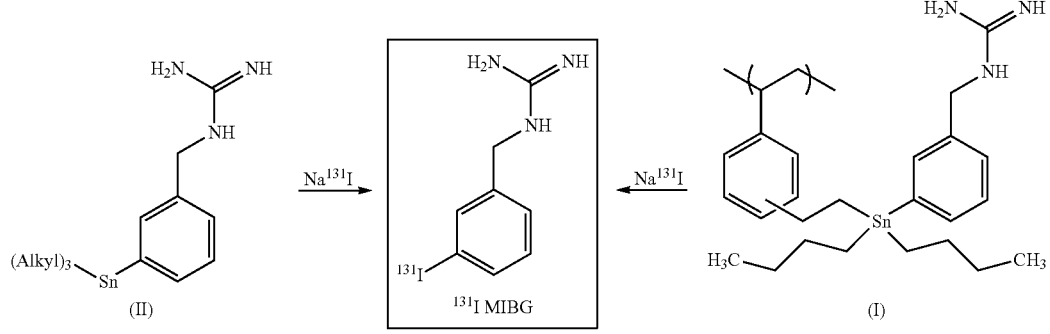

In some aspects, provided are preparations of polymers comprising monomer of formula (I):

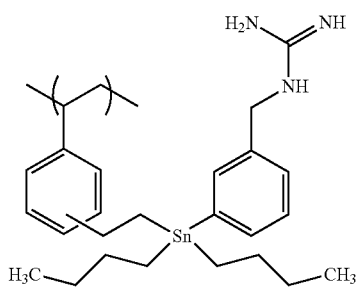

(I)

or pharmaceutically acceptable salts thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, preparations of polymer as described herein include one or more monomers in a salt form and, in particular, in a pharmaceutically acceptable salt form (e.g., comprising a pharmaceutically acceptable salt of an amino group). In some embodiments, a pharmaceutically acceptable salt is a hydrochloric acid (HCl) salt, yielding polymer comprising monomer of formula (Ia). In some embodiments, a pharmaceutically acceptable salt is an acetic acid (HOAc) salt, yielding polymer comprising monomer of formula (Ib).

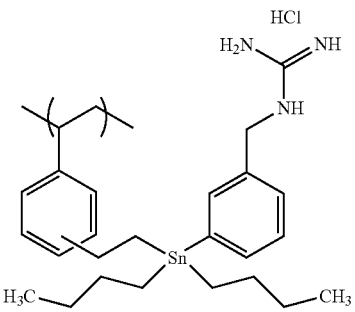

(Ia)

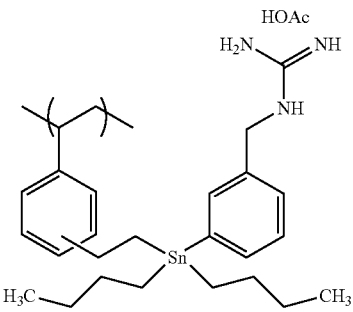

(Ib)

In some embodiments, polymers as described herein comprise, at least in part, homopolymeric segments as set forth in formula (III):

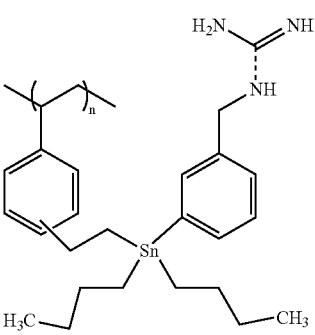

(III)

wherein n is 2 to 1,000,000. In some embodiments, n is 100 to 100,000. In some embodiments, n is 500 to 100,000. In some embodiments, n is 500 to 50,000. In some embodiments, n is 500 to 10,000. In some embodiments, n is 500 to 1,000. In some embodiments, n is 100 to 500. In some embodiments, n is 2 to 100. In some embodiments, the polymer is crosslinked.

Reduced Levels of Leachable Tin

Technologies provided herein permit preparation and/or maintenance of polymer preparations having low levels of leachable tin. In some embodiments, provided polymer preparations have reduced levels of leachable tin as compared with compositions reliably obtained using prior technologies including, for example, as set forth in the University Patent.

As used herein, the terms "leachable tin," "leachable tin-containing side products" and "tin-containing fragments" are used interchangeably and refer to tin salts or tin-containing compounds that are soluble in, or miscible with, water (e.g., aqueous solutions) or organic solvents (e.g., methanol, ethanol, diethyl ether, tetrahydrofuran, dichloromethane, hexane, acetone, toluene, or acetonitrile). For example, the leachable tin components referred to herein may include tin-containing fragments from the polymer comprising monomer of formula (I) that wash from the polymer upon treatment or washing with water and/or organic solvents. In some embodiments of the polymer comprising monomer of formula (I), the leachable tin-containing side products have a molecular weight of less than 2,000 Daltons. In some embodiments, the leachable tin-containing side products have a molecular weight less than 1,000 Daltons. In some embodiments, the leachable tin-containing side products have a molecular weight less than 500 Daltons. In some embodiments, at least some of the leachable tin-containing side products include a di-butyl-tin-containing substituent.

In some embodiments, provided polymer preparations have leachable tin at a level within a range of about 0 ppm to about 850 ppm. In some embodiments, provided polymer preparations have leachable tin at a level below about 850 ppm. In some embodiments, provided polymer preparations have leachable tin at a level below about 800 ppm. In some embodiments, provided polymer preparations have leachable tin at a level below about 750 ppm. In some embodiments, provided polymer preparations have leachable tin at a level below about 700 ppm. In some embodiments, provided polymer preparations have leachable tin at a level below about 650 ppm. In some embodiments, provided polymer preparations have leachable tin at a level below about 600 ppm. In some embodiments, provided polymer preparations have leachable tin at a level below about 550 ppm. In some embodiments, provided polymer preparations have leachable tin at a level below about 500 ppm. In some embodiments, provided polymer preparations have leachable tin at a level below about 450 ppm. In some embodiments, provided polymer preparations have leachable tin at a level below about 400 ppm. In some embodiments, provided polymer preparations have leachable tin at a level below about 350 ppm. In some embodiments, provided polymer preparations have leachable tin at a level below about 300 ppm. In some embodiments, provided polymer preparations have leachable tin at a level below about 250 ppm. In some embodiments, provided polymer preparations have leachable tin at a level below about 200 ppm. In some embodiments, provided polymer preparations have leachable tin at a level below about 150 ppm. In some embodiments, provided polymer preparations have leachable tin at a level within a range of about 0 ppm to about 150 ppm. In some embodiments, the preparation comprising the polymer comprising monomer of formula (I) includes leachable tin at a level of 0 ppm to 140 ppm. In some embodiments, the preparation includes leachable tin at a level of 0 ppm to 130 ppm. In some embodiments, the preparation includes leachable tin at a level of 0 ppm to 120 ppm. In some embodiments, the preparation includes leachable tin at a level of 0 ppm to 110 ppm. In some embodiments, the preparation includes leachable tin at a level of 0 ppm to 100 ppm. In some embodiments, the preparation includes leachable tin at a level of 0 ppm to 90 ppm. In some embodiments, the preparation includes leachable tin at a level of 0 ppm to 80 ppm. In some embodiments, the preparation includes leachable tin at a level of 0 ppm to 70 ppm. In some embodiments, the preparation includes leachable tin at a level of 0 ppm to 60 ppm. In some embodiments, the preparation includes leachable tin at a level of 0 ppm to 50 ppm. In some embodiments, the preparation includes leachable tin at a level of 0 ppm to 40 ppm. In some embodiments, the preparation includes leachable tin at a level of 0 ppm to 30 ppm. In some embodiments, the preparation includes leachable tin at a level of 0 ppm to 20 ppm. In some embodiments, the preparation includes leachable tin at a level of 0 ppm to 10 ppm.

Applicants have discovered that levels of leachable tin in the polymers comprising a monomer of formula (I) can increase with time and/or upon exposure to one or more of moisture, temperature and $O_2$. In some embodiments, provided polymer preparations as described herein with reduced levels of leachable tin maintain their reduced levels of leachable tin for extended periods of time under appropriate storage conditions. In some embodiments, provided polymer preparations as described herein are subject to levels of leachable tin that increase with time, but significantly less so and/or at a lower rate, than known polymer preparations (e.g., those of U.S. Pat. No. 7,658,910) produce levels of leachable tin with time.

In some particular embodiments, provided polymer preparations maintain a reduced level of tin when stored at −20° C.; in some such embodiments, the reduced level of tin is a level of less than about 850 ppm, less than about 800 ppm, less than about 750 ppm, less than about 700 ppm, less than about 650 ppm, less than about 600 ppm, less than about 550 ppm, less than about 500 ppm, less than about 450 ppm, less than about 400 ppm, less than about 350 ppm, less than about 300 ppm, less than about 250 ppm, less than about 200 ppm, less than about 150 ppm, less than about 100 ppm, less than about 90 ppm, less than about 80 ppm, less than about 70 ppm, less than about 60 ppm, less than about 50 ppm, less than about 40 ppm, less than about 30 ppm, less than about 20 ppm, and/or less than about 10 ppm for a period of time that is at least 6 months, at least 1 year, at least 2 years, at least 3 years, or more.

In some embodiments, provided polymer preparations have leachable tin at a level below about 850 ppm, 800 ppm, 750 ppm, 700 ppm, 650 ppm, 600 ppm, 550 ppm, 500 ppm, 450 ppm, 400 ppm, 350 ppm, 300 ppm, 250 ppm, 200 ppm, 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm, 5 ppm or less for at least 6 months at about 40° C., 20° C., 0° C., −10° C. or −20° C. In some embodiments, the provided polymer preparations are stored about 1 month to about 6 months, or about 6 months, at any one or between any two of the above-indicated temperatures under an inert gas such as $N_2$. In some embodiments, the provided polymer preparations are stored about 1 month to about 6 months, or about 6 months, at any one or between any two of the above-indicated temperatures under air having a relative humidity of 1% to 25%, 25% to 50%, 50% to 75%, 75% to 90%, or higher. In some embodiments, the provided polymer preparations are stored about 1 month to about 6 months, or about 6 months, at any one or between any two of the above-indicated temperatures under air having a relative humidity of about 60%. In some embodiments, the provided polymer preparations are stored about 1 month to about 6 months, or about 6 months, at any one or between any two of the above-indicated temperatures under air having a relative humidity of about 75%.

In some embodiments, provided polymer preparations have leachable tin at a level below about 850 ppm, 800 ppm, 750 ppm, 700 ppm, 650 ppm, 600 ppm, 550 ppm, 500 ppm, 450 ppm, 400 ppm, 350 ppm, 300 ppm, 250 ppm, 200 ppm, 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm, 5 ppm or less for at least 1 year at about 40° C., 20° C., 0° C., −10° C. or −20° C. In some embodiments, the provided polymer preparations are stored about 6 months to about 1 year, or about 1 year, at any one or between any two of the above-indicated temperatures under an inert gas such as $N_2$. In some embodiments, the provided polymer preparations are stored about 6 months to about 1 year, or about 1 year, at any one or between any two of the above-indicated temperatures under air having a relative humidity of 1% to 25%, 25% to 50%, 50% to 75%, 75% to 90%, or higher. In some embodiments, the provided polymer preparations are stored about 6 months to about 1 year, or about 1 year, at any one or between any two of the above-indicated temperatures under air having a relative humidity of about 60%. In some embodiments, the provided polymer preparations are stored about 6 months to about 1 year, or about 1 year, at any one or between any two of the above-indicated temperatures under air having a relative humidity of about 75%.

In some embodiments, provided polymer preparations have leachable tin at a level below about 850 ppm, 800 ppm, 750 ppm, 700 ppm, 650 ppm, 600 ppm, 550 ppm, 500 ppm, 450 ppm, 400 ppm, 350 ppm, 300 ppm, 250 ppm, 200 ppm, 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm, 5 ppm or less for at least 2 years at about 40° C., 20° C., 0° C., −10° C. or −20° C. In some embodiments, the provided polymer preparations are stored about 1 year to about 2 years, or about 2 years, at any one or between any two of the above-indicated temperatures under an inert gas such as $N_2$. In some embodiments, the provided polymer preparations are stored about 1 year to about 2 years, or about 2 years, at any one or between any two of the above-indicated temperatures under air having a relative humidity of 1% to 25%, 25% to 50%, 50% to 75%, 75% to 90%, or higher. In some embodiments, the provided polymer preparations are stored about 1 year to about 2 years, or about 2 years, at any one or between any two of the above-indicated temperatures under air having a relative humidity of about 60%. In some embodiments, the provided polymer preparations are stored about 1 year to about 2 years, or about 2 years, at any one or between any two of the above-indicated temperatures under air having a relative humidity of about 75%.

In some embodiments, provided polymer preparations have leachable tin at a level below about 850 ppm, 800 ppm, 750 ppm, 700 ppm, 650 ppm, 600 ppm, 550 ppm, 500 ppm, 450 ppm, 400 ppm, 350 ppm, 300 ppm, 250 ppm, 200 ppm, 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm, 5 ppm or less for at least 3 years at about 40° C., 20° C., 0° C., −10° C. or −20° C. In some embodiments, the provided polymer preparations are stored about 2 years to about 3 years, or about 3 years, at any one or between any two of the above-indicated temperatures under an inert gas such as $N_2$. In some embodiments, the provided polymer preparations are stored about 2 years to about 3 years, or about 3 years, at any one or between any two of the above-indicated temperatures under air having a relative humidity of 1% to 25%, 25% to 50%, 50% to 75%, 75% to 90%, or higher. In some embodiments, the provided polymer preparations are stored about 2 years to about 3 years, or about 3 years, at any one or between any two of the above-indicated temperatures under air having a relative humidity of about 60%. In some embodiments, the provided polymer preparations are stored about 2 years to about 3 years, or about 3 years, at any one or between any two of the above-indicated temperatures under air having a relative humidity of about 75%.

Inert Atmosphere

Applicants have found that exposure of a polymer comprising monomer of formula (I), and/or of tin-containing synthetic precursors thereof, to air and/or $O_2$ can degrade tin-containing fragments from the polymer and increase levels of leachable tin in polymer preparations. This finding embodies the identification of the source of a problem with certain prior preparation technologies.

In light of this finding, Applicants have recognized that maintaining polymer preparations as described herein under inert atmospheric conditions can provide certain desirable and beneficial advantages. Accordingly, in some embodiments, the present disclosure provides polymer preparations maintained under inert gas (e.g., enclosed in a container under inert gas). In some embodiments the inert gas is nitrogen. In some embodiments the inert gas is argon.

Reduced Moisture

Applicants have further discovered that exposure of a polymer comprising monomer of formula (I), and/or of tin-containing synthetic precursors thereof, to moisture can degrade tin-containing fragments from the polymer and increase levels of leachable tin in polymer preparations. Accordingly, in some embodiments, the present disclosure provides polymer preparations containing less than 2.0 wt % water, e.g., relative to the wt % of polymer in the preparation. In some embodiments, the present disclosure provides polymer preparations containing less than 1.5 wt % water, less than about 1.4 wt % water, less than about 1.3 wt % water, less than about 1.2 wt % water, less than about 1.1 wt % water, less than about 1.0 wt % water, less than about 0.9 wt % water, less than about 0.8 wt % water, less than about 0.7 wt % water, less than about 0.6 wt % water, less than about 0.5 wt % water, less than about 0.4 wt % water, less than about 0.3 wt % water, less than about 0.2 wt % water, or less than about 0.1 wt % water, or less than about 0.05 wt % water, e.g., relative to the wt % of polymer in the preparation.

Solvent-Free

Applicants have also discovered that exposure of the polymer comprising monomer of formula (I), and tin-containing synthetic precursors thereof, to organic solvents (e.g., methanol, ethanol, diethyl ether, tetrahydrofuran, dichloromethane, hexane, acetone, toluene, or acetonitrile) can degrade tin-containing fragments from the polymer and increase the levels of leachable tin. In some embodiments, the preparation comprising the polymer comprising monomer of formula (I) contain less than about 0.5 wt % organic solvents, e.g., relative to the wt % of polymer in the preparation. In some embodiments, the preparation comprises less than about 0.4 wt % organic solvents, less than about 0.3 wt % organic solvents, less than about 0.2 wt % organic solvents, or less than about 0.1 wt % organic solvents, e.g., relative to the wt % of polymer in the preparation.

Pure and/or Stable Polymers

The insights and technologies provided in the present disclosure permit production and/or maintenance of, and thus provide, substantially pure polymer preparations.

For example, in some embodiments, the present invention provides substantially pure preparations of polymers comprising monomers of formula (I), or salts thereof. In some embodiments, a pure preparation is characterized in that at least 90 wt % of the monomers in the preparation have the structure of formula (I), or a salt thereof. In some embodiments, at least 95 wt %, at least 96 wt %. at least 97 wt %, at least 98 wt %, at least 99 wt %, at least 99.5 wt % or more of the monomers in the preparation have the structure of formula (I), or a salt thereof.

In some embodiments, the present disclosure provides pure polymer preparations that are stable for extended periods of time in that the percentage of monomers having the structure of formula (I), or salts thereof, remains above a designated level as set forth above, over a designated period of time under selected conditions.

In some embodiments, the preparation comprises at least 95 wt % of the polymer comprising monomer of formula (I), or salt thereof, for at least 6 months at −20° C. In some embodiments, the preparation comprises at least 95 wt % of the polymer comprising monomer of formula (I), or salt thereof, for at least 1 year at −20° C. In some embodiments, the preparation comprises at least 95 wt % of the polymer comprising monomer of formula (I), or salt thereof, for at least 2 years at −20° C. In some embodiments, the preparation comprises at least 95 wt % of the polymer comprising monomer of formula (I), or salt thereof, for at least 3 years at −20° C.

In other related embodiments, the preparation comprises at least 98 wt % of the polymer comprising monomer of formula (I), or salt thereof, for at least 6 months at −20° C. In some embodiments, the preparation comprises at least 98 wt % of the polymer comprising monomer of formula (I), or salt thereof, for at least 1 year at −20° C. In some embodiments, the preparation comprises at least 98 wt % of the polymer comprising monomer of formula (I), or salt thereof, for at least 2 years at −20° C. In some embodiments, the preparation comprises at least 98 wt % of the polymer comprising monomer of formula (I), or salt thereof, for at least 3 years at −20° C.

In some embodiments, polymer preparations (e.g., pure polymer preparations) as provided herein are substantially free of unintended side-product polymers comprising monomers formula (I). In some specific embodiments, such provided polymer preparations are substantially free of monomers of formulae (IV) and/or (V):

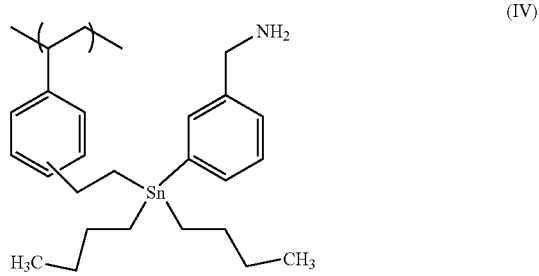

(IV)

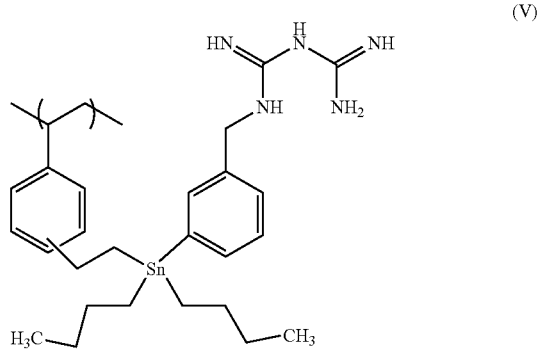

(V)

or pharmaceutically acceptable salts thereof, and/or of polymers that comprise them.

In some embodiments, provided polymer preparations contain less than about a maximum level of monomers of formula (IV), monomers of formula (V), or both, or pharmaceutically acceptable salts thereof. In some embodiments, the maximum level is about 0.5 wt %. That is, in some embodiments, the present invention provides polymer preparations in which monomers having the structure of formula (IV), or pharmaceutically acceptable salts thereof, are present at a level below about 0.5 wt %, relative to the wt % of the monomers having the structure of formula (I) in the polymer. In some embodiments, the present invention provides polymer preparations in which monomers having the structure of formula (V), or pharmaceutically acceptable salts thereof, are present at a level below about 0.5 wt %, relative to the wt % of the monomers having the structure of formula (I) in the polymer. In some embodiments, the present invention provides polymer preparations in which monomers having the structure of formula (IV) or formula (V), or pharmaceutically acceptable salts thereof, are present at a level below about 0.5 wt %, relative to the wt % of the monomers having the structure of formula (I) in the polymer. In some embodiments, the maximum level is about 0.4%, 0.3%, 0.2%, 0.1%, or less.

In some embodiments, the present invention provides polymer preparations comprising monomers of formula (I), wherein at least 90%, 95%, 96%, 97%, 98%, or 99% or more of the monomers in the polymer are of formula (I). In some embodiments, the present invention provides polymer preparations comprising monomers of formula (I), wherein not more than 0.5%, 0.4%, 0.3%, 0.2%, 0.1%, or less of the monomers in the polymer are of formula (IV) or formula (V).

Kits

As described herein, Applicants have found that exposure of polymers comprising monomers of formula (I), and/or tin-containing synthetic precursors thereof, to air, O$_2$, moisture, organic solvents and/or ambient or increased temperature can degrade tin-containing fragments from the polymer and increase levels of leachable tin in polymer preparations. Among other things, Applicants have developed strategies for maintaining polymer preparations under conditions that minimize such degradation.

For example, in some embodiments, the present invention provides technologies for storing polymer preparations under inert gas for part or all of the time from its production until it is used to prepare and/or converted into MIBG. Thus, in some embodiments, the present invention provides preparations of polymers comprising monomers having the structure of formula (I):

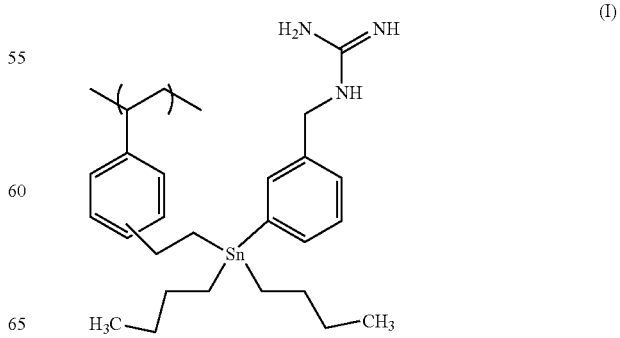

(I)

or a pharmaceutically acceptable salt thereof, wherein polymers in the preparations include n monomers, the preparations having a reduced level of leachable tin, which reduced level is between about 0 ppm to about 150 ppm, the preparations being provided in a kit that further comprises one or more containers that store the polymer preparations under inert gas.

In some embodiments, provided kits may comprise any of the polymer preparations as described herein.

In some embodiments, the pharmaceutically acceptable salt is a hydrochloric acid (HCl) salt. In other embodiments, the pharmaceutically acceptable salt is an acetic acid (HOAc) salt.

In some embodiments, containers included in provided kits store polymer preparations under nitrogen. In some embodiments, containers included in provided kits store polymer preparations under argon.

In some embodiments, containers included in provided kits are glass vials. In some embodiments, the glass vials are made from Type I borosilicate glass or Type III soda lime glass. In some embodiments, the glass vials are colored, such as green or amber. In some embodiments, the glass vials have a volume of about 0.1 mL-1.0 mL, 1.0 mL-2.0 mL, 2.0 mL-5.0 mL, 5.0 mL-10.0 mL, 10.0 mL-20.0 mL, 20.0 mL-30.0 mL, 20.0 mL-40.0 mL, 40.0 mL-50.0 mL, or greater. In some embodiments, the glass vials have a volume of about 2.0 mL. In some embodiments, the glass vials have a height of about 10-50 mm. In some embodiments, the glass vials have a height of about 30-40 mm. In some embodiments, the glass vials may have a height of about 35 mm. In some embodiments, the glass vials have an inner diameter of about 5-10 mm. In some embodiments, the glass vials have an inner diameter of about 7-8 mm. In some embodiments, the glass vials have an outer diameter of about 5-25 mm. In some embodiments, the glass vials have an outer diameter of about 10-20 mm. In some embodiments, the glass vials have an outer diameter of about 12-13 mm. In some embodiments, the glass vials have an outer diameter of about 16 mm.

In some embodiments, containers included in provided kits are glass vials having a polymeric or rubber (e.g., synthetic rubber) stopper or closure that seals the vial and substantially prevents an escape of inert gas, such as nitrogen, from within the sealed vial. In some embodiments, the polymeric stopper is made from synthetic rubber. In some embodiments, the polymeric stopper is made from bromobutyl polymer. In some embodiments, the polymeric stopper, such as a bromobutyl stopper, is coated with a fluorinated polymer coating, that may be applied to the stopper, for example, via spray-dry coating process, to render the coated stopper substantially chemically inert.

In some embodiments, the container, such as a glass vial, included in provided kit, is sealed with a rubber septum that substantially prevents an escape of inert gas, such as nitrogen, from within the sealed vial. In some embodiments, containers included in provided kits are amber glass vials made from Type I borosilicate glass, having a volume of about 2.0 mL, a height of about 35 mm, and outer diameter between about 12-16 mm. In some embodiments, the above-described amber glass vials are sealed with a polymeric stopper made from bromobutyl polymer, where the stopper is coated with a fluorinated polymer coating, the coating having a thickness of about 10 µm to about 20 µm. In some embodiments, the rubber septum is fastened to the glass vial via and aluminum seal.

In some embodiments, provided kits, and/or containers included therein, include a means, such as dry ice, or a refrigeration unit, to cool the kit below ambient temperature (e.g., 20° C., 0° C., −10° C. or −20° C.).

In some embodiments, provided kits comprise instructions for use.

In some embodiments, provided kits permit storage of polymer preparations as described herein over extended periods of time while preserving their stability (e.g., with respect to level of leachable tin levels and/or with respect to unintended side-products e.g., as described herein). In some embodiments, stability is preserved at −20° C. for a period of time that is at least 6 months, at least 1 year at least 2 years, at least 3 years, or more.

In some embodiments, provided kits preserve stability with respect to minimum percentage of monomers having the structure of formula (I), or a pharmaceutically acceptable salt thereof, in a polymer preparation. In some embodiments, such percentage is at least 96%, 96%, 97%, 98%, 99%, 99.5%, or more.

In some embodiments, provided kits preserve stability with respect to maximal level of one or more unintended side products. For example, in some embodiments, provided kits preserve stability with respect to maximum percentage of monomers having the structure of formula (IV), or pharmaceutically acceptable salts thereof and/or to maximum percentage of monomers having the structure of formula (V), or pharmaceutically acceptable salts thereof, or both. In some embodiments, such maximal percentage is less than about 0.5%, less than about 0.4%, less than about 0.3%, less than about 0.2%, less than about 0.1%, or less.

In some embodiments, provided kits preserve stability with respect to maximal level of leachable tin content. In some embodiments, such maximum level is less than about 150 ppm less than about 100 ppm, less than about 50 ppm less than about 25 ppm, or less.

In some embodiments of the kit, polymer preparations have leachable tin at a level below about 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm, 5 ppm or less for at least 6 months at −20° C.

In some embodiments of the kit, polymer preparations have leachable tin at a level below about 20 ppm for at least 6 months at −20° C.

In some embodiments of the kit, polymer preparations have leachable tin at a level below about 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm, 5 ppm or less for at least 9 months at −20° C.

In some embodiments of the kit, polymer preparations have leachable tin at a level below about 20 ppm for at least 9 months at −20° C.

In some embodiments of the kit, polymer preparations have leachable tin at a level below about 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm, 5 ppm or less for at least 1 year at −20° C.

In some embodiments of the kit, polymer preparations have leachable tin at a level below about 20 ppm for at least 1 year at −20° C.

In some embodiments of the kit, polymer preparations have leachable tin at a level below about 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm, 5 ppm or less for at least 2 years at −20° C.

In some embodiments of the kit, polymer preparations have leachable tin at a level below about 20 ppm for at least 2 years at −20° C.

In some embodiments of the kit, polymer preparations have leachable tin at a level below about 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm, 5 ppm or less for at least 3 years at −20° C.

In some embodiments of the kit, polymer preparations have leachable tin at a level below about 20 ppm for at least 3 years at −20° C.

In some embodiments of the kit, the polymer preparations contain water at a level of less than 2.0 wt % water, e.g., relative to the wt % of polymer in the preparation. In some embodiments, the polymer preparations contain less than 1.5 wt % water, less than about 1.4 wt % water, less than about 1.3 wt % water, less than about 1.2 wt % water, less than about 1.1 wt % water, less than about 1.0 wt % water, less than about 0.9 wt % water, less than about 0.8 wt % water, less than about 0.7 wt % water, less than about 0.6 wt % water, less than about 0.5 wt % water, less than about 0.4 wt % water, less than about 0.3 wt % water, less than about 0.2 wt % water, or less than about 0.1 wt % water, or less than about 0.05 wt % water, e.g., relative to the wt % of polymer in the preparation.

MIBG Compositions and Compositions Comprising a Compound of Formula (VI)

Among other things, the present invention provides technologies, for example utilizing polymer preparations as described herein, for the production of MIBG compositions, and compositions comprising a compound of formula (VI):

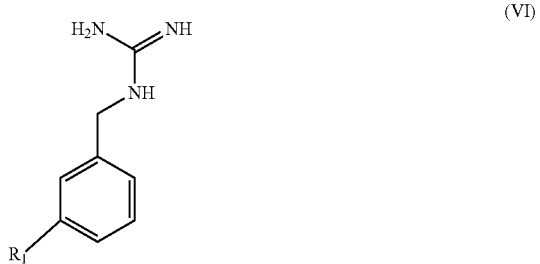

or pharmaceutically acceptable salts thereof, wherein $R_1$ is a radioisotopic label.

As used herein, the term "radioisotopic label" of $R_1$ is intended to mean a radioisotope of an atom or ion that enables detection of the compound or composition that includes the radioisotopic label. The radioisotopic label, includes, but is not limited to, a radiohalogen isotope (i.e., atom or ion) including any one of fluoride ($^{18}$F), bromide ($^{74}$Br, $^{75}$Br, $^{76}$Br, $^{77}$Br, $^{78}$Br, $^{80}$Br $^{82}$Br, $^{83}$Br, $^{84}$Br, $^{85}$Br, $^{86}$Br, $^{87}$Br, $^{88}$Br, $^{89}$Br or $^{90}$Br), iodide ($^{123}$I, $^{124}$I, $^{125}$I, $^{131}$I), or astatine ($^{209}$At, $^{210}$At or $^{211}$At).

In some embodiments, $R_1$ is $^{18}$F.

In some embodiments, $R_1$ is $^{74}$Br, $^{75}$Br, $^{76}$Br, $^{77}$Br, $^{78}$Br, $^{80}$Br, $^{82}$Br, $^{83}$Br, $^{84}$Br, $^{85}$Br, $^{86}$Br, $^{87}$Br, $^{88}$Br, $^{89}$Br or $^{90}$Br.

In some embodiments, $R_1$ is $^{123}$I, $^{124}$I $^{125}$I, $^{131}$I. In some embodiments, $R_1$ is $^{123}$I. In some embodiments, $R_1$ is $^{124}$I. In some embodiments, $R_1$ is $^{125}$I. In some embodiments, $R_1$ is $^{131}$I. In some embodiments, $R_1$ is $^{123}$I. In some embodiments, $R_1$ is $^{131}$I.

In some embodiments, $R_1$ is $^{209}$At, $^{210}$At or $^{211}$At. In some embodiments, $R_1$ is $^{209}$At. In some embodiments, $R_1$ is $^{210}$At. In some embodiments, $R_1$ is $^{211}$At.

According to some aspects, provided are pharmaceutical compositions comprising MIBG, or the compound of formula (VI), or a pharmaceutically acceptable salt thereof, and a pharmaceutically acceptable carrier, adjuvant, or vehicle, wherein the MIBG is formed by contacting iodine or an iodide salt with a polymer preparation as described herein i.e., of polymers comprising monomers of formula (I):

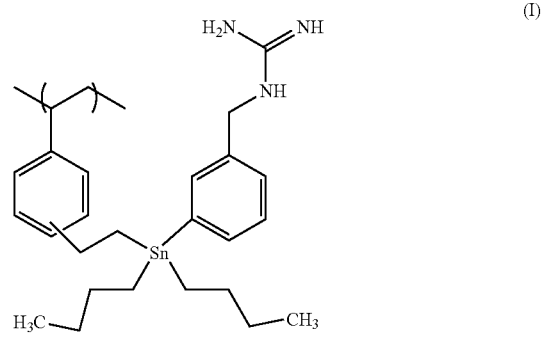

or a pharmaceutically acceptable salt thereof. In some embodiments, the polymer preparation comprises leachable tin at a level of 0 ppm to 150 ppm.

In some embodiments, the polymer preparation has leachable tin at a level below about 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm or 5 ppm.

According to further aspects, provided is a pharmaceutical composition comprising the compound of formula (VI):

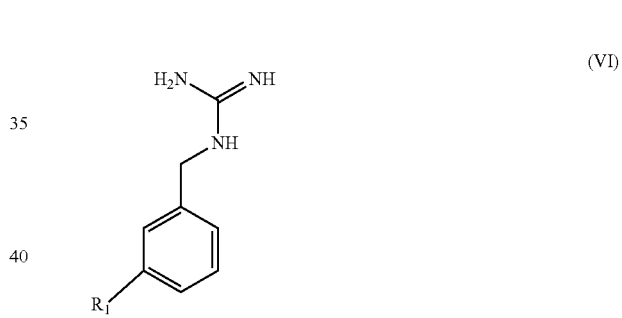

or a pharmaceutically acceptable salt thereof, and a pharmaceutically acceptable carrier, adjuvant, or vehicle, wherein $R_1$ is a radioisotopic label, and the pharmaceutical composition comprises leachable tin at a level of 0 ppm to 150 ppm.

In some embodiments, provided is a pharmaceutical composition comprising meta-iodobenzylguanidine (MIBG):

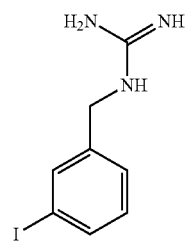 [SMILES: N=C(N)NCc1cccc(I)c1]

or a pharmaceutically acceptable salt thereof, and a pharmaceutically acceptable carrier, adjuvant, or vehicle, wherein the pharmaceutical composition comprises leachable tin at a level of 0 ppm to 150 ppm.

In some embodiments, the pharmaceutical composition, comprising MIBG, or the compound of formula (VI) or a pharmaceutically acceptable salt thereof, has leachable tin at a level below about 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm or 5 ppm.

Described herein are methods for characterizing levels of leachable tin in any of the polymer preparations disclosed herein, and for characterizing levels of leachable tin in any of the disclosed pharmaceutical compositions comprising the compound of formula (VI) or MIBG. In some embodiments, such methods include the use of inductively coupled plasma mass spectrometry (ICP-MS). Such methods are described in greater detail in the Examples below. Applicants note that methods for characterizing levels of leachable tin in any of the disclosed pharmaceutical compositions may conveniently be conducted upon compositions comprising non-radioisotopic analogs of compounds of formula (VI) or MIBG. For example, a polymer comprising monomers of formula (I) may be contacted with non-radioisotopic iodine or iodide to form non-radioisotopic MIBG, which can safely be subjected to analytical methods such as ICP-MS to quantify levels of leachable tin in the non-radioisotopic MIBG composition. Such levels can readily be correlated to compositions comprising radioisotopic MIBG formed from radioisotopic iodide.

In some embodiments, the compound of formula (VI) is formed by contacting a radioisotope of a halogen ion with a polymer preparation as described herein i.e., of polymers comprising monomers of formula (I).

In certain embodiments of provided MIBG compositions, the MIBG is formed by contacting the iodide salt with a polymer preparation provided herein.

In certain embodiments of provided compositions comprising the compound of formula (VI), the compound of formula (VI) is formed by contacting a radioisotope of fluoride, bromide, iodide or astatine with a polymer preparation provided herein.

In certain embodiments, provided MIBG compositions, or compositions comprising the compound of formula (VI), are formulated for administration to a patient in need thereof.

In some embodiments of the pharmaceutical composition, the iodide salt is sodium iodide. In other embodiments, the iodide salt is sodium I-123 iodide. In some embodiments the iodide salt is sodium I-131 iodide.

In some embodiments, provided MIBG compositions, or compositions comprising the compound of formula (VI), are formulated for intravenous administration to a patient.

In some embodiments, provided MIBG compositions, or compositions comprising the compound of formula (VI), are formulated as an Imaging Dose to provide 1-50 mCi/kg, 5-30 mCi/kg, 10-25 mCi/kg or about 3-6 mCi/kg of radioactivity (e.g., of I-131 or At-211), for example, upon intravenous administration to a patient in need thereof. In some embodiments, the Imaging Dose is used, for example, to determine if a patient meets radiological entry criteria and/or to establish dosimetry for the subject.

In some embodiments, provided MIBG compositions, or compositions comprising the compound of formula (VI), are formulated as a Therapeutic Dose to provide 50-1,000 mCi/kg, 100-800 mCi/kg, 400-600 mCi/kg or about 500 mCi of radioactivity (e.g., of I-131 or At-211), for example, upon intravenous administration to a patient in need thereof. In some embodiments, the Therapeutic Dose is followed by imaging of the patient within 7 days post infusion. In some embodiments, the Therapeutic Dose is optionally adjusted equally if warrented by results of a dosimetry evaluation. In some embodiments, the patient will receive a second Therapeutic Dose of MIBG at least 2, 3, 4 or more months later.

The term "patient," as used herein, means an animal, preferably a mammal, and most preferably a human. In some embodiments, the patient is in need of treatment for malignant pheochromocytoma, a rare, hard-to-access neuroendocrine tumor that develops in the core of an adrenal gland. In some embodiments, the patient is in need of treatment for neuroendocrine tumors (NETs), rare tumors of the nervous and endocrine systems. In some embodiments, the NET is neuroblastoma, the most common extracranial solid cancer in childhood and the most common cancer in infancy. In some embodiments, the patient is a child in need of treatment for neuroblastoma. In other embodiments, the patient is an adult in need of treatment for pheochromocytoma, a neuroendocrine tumor of the medulla of the adrenal glands.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, the pharmaceutical composition comprising MIBG, or a pharmaceutically acceptable salt thereof, particularly an acetic acid (HOAc) salt thereof, formed by contacting the iodide salt with any of the above disclosed preparations of a polymer comprising monomer of formula (I), may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent.

In some embodiments, the sterile injectable preparation comprises MIBG at a concentration of 0.0001-0.1 mg/mL. In some embodiments, the sterile injectable preparation comprises MIBG at a concentration of 0.001-0.01 mg/mL. In some embodiments, the sterile injectable preparation has a radiochemical purity >90% or >95%. In some embodiments, the sterile injectable preparation comprises gentisate, for example, at a concentration of 2-200 mg/mL or 20-25 mg/mL. In some embodiments, the sterile injectable preparation comprises ascorbate, for example, at a concentration of 2-200 mg/mL or 48-64 mg/mL. In some embodiments, the sterile injectable preparation comprises gentisate. In some embodiments, the sterile injectable preparation has a pH of 3-7. In some embodiments, the sterile injectable preparation has a pH of 4-6. In some embodiments, the sterile injectable preparation has a pH of 4.5-5.5.

In some embodiments, provided MIBG compositions (e.g., formed by contacting the iodide salt with a provided polymer preparation), or compositions comprising the compound of formula (VI), are substantially free of (e.g., comprise less than 2 wt % of) meta-iodobenzylamine (MIBA), meta-iodobenzylbiguanidine (MIBBG), and/or meta-hydroxybenzylguanidine (MHBG).

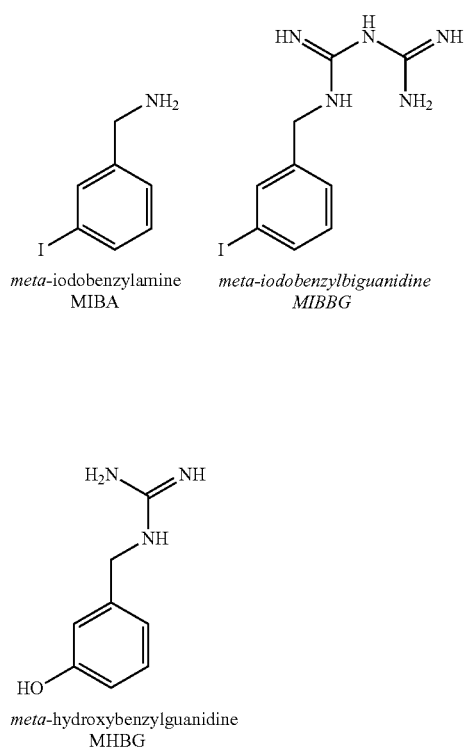

meta-iodobenzylamine
MIBA meta-iodobenzylbiguanidine
MIBBG meta-hydroxybenzylguanidine
MHBG In some embodiments, provided MIBG pharmaceutical compositions, or pharmaceutical compositions comprising the compound of formula (VI), contain less than about 1.0 wt % MIBA, relative to the wt % of the MIBG. In some embodiments, the composition comprising MIBG, or compositions comprising the compound of formula (VI), contain less than about 0.5 wt % MIBA. In some embodiments, the composition comprising MIBG, or compositions comprising the compound of formula (VI), contain less than about 0.4 wt % MIBA. In some embodiments, the composition comprising MIBG, or compositions comprising the compound of formula (VI), contain less than about 0.3 wt % MIBA. In some embodiments, the composition comprising MIBG, or compositions comprising the compound of formula (VI), contain less than about 0.2 wt % MIBA. In some embodiments, the composition comprising MIBG, or compositions comprising the compound of formula (VI), contain less than about 0.1 wt % MIBA.

In some embodiments, the pharmaceutical composition comprising MIBG, or pharmaceutical compositions comprising the compound of formula (VI), contain less than about 1.0 wt % MIBBG, relative to the wt % of the MIBG. In some embodiments, the composition comprising MIBG, or compositions comprising the compound of formula (VI), contain less than about 0.5 wt % MIBBG. In some embodiments, the composition comprising MIBG, or compositions comprising the compound of formula (VI), contain less than about 0.4 wt % MIBBG. In some embodiments, the composition comprising MIBG, or compositions comprising the compound of formula (VI), contain less than about 0.3 wt % MIBBG. In some embodiments, the composition comprising MIBG, or compositions comprising the compound of formula (VI), contain less than about 0.2 wt % MIBBG. In some embodiments, the composition comprising MIBG, or compositions comprising the compound of formula (VI), contain less than about 0.1 wt % MIBBG.

In some embodiments, the pharmaceutical composition comprising MIBG, or pharmaceutical compositions comprising the compound of formula (VI), contain less than about 1.0 wt % MHBG, relative to the wt % of the MIBG. In some embodiments, the composition comprising MIBG, or compositions comprising the compound of formula (VI), contain less than about 0.5 wt % MHBG. In some embodiments, the composition comprising MIBG, or compositions comprising the compound of formula (VI), contain less than about 0.4 wt % MHBG. In some embodiments, the composition comprising MIBG, or compositions comprising the compound of formula (VI), contain less than about 0.3 wt % MHBG. In some embodiments, the composition comprising MIBG, or compositions comprising the compound of formula (VI), contain less than about 0.2 wt % MHBG. In some embodiments, the composition comprising MIBG, or compositions comprising the compound of formula (VI), contain less than about 0.1 wt % MHBG.

In some embodiments, the pharmaceutical composition comprising MIBG, or pharmaceutical compositions comprising the compound of formula (VI), contain less than about 1.0 wt % MIBA, MIBBG and/or MHBG, relative to the wt % of the MIBG. In some embodiments, the composition comprising MIBG, or compositions comprising the compound of formula (VI), contain less than about 0.5 wt % MIBA, MIBBG and/or MHBG. In some embodiments, the composition comprising MIBG, or compositions comprising the compound of formula (VI), contain less than about 0.4 wt % MIBA, MIBBG and/or MHBG. In some embodiments, the composition comprising MIBG, or compositions comprising the compound of formula (VI), contain less than about 0.3 wt % MIBA, MIBBG and/or MHBG. In some embodiments, the composition comprising MIBG, or compositions comprising the compound of formula (VI), contain less than about 0.2 wt % MIBA, MIBBG and/or MHBG. In some embodiments, the composition comprising MIBG, or compositions comprising the compound of formula (VI), contain less than about 0.1 wt % MIBA, MIBBG and/or MHBG.

Polymer Synthesis and Purification

In certain embodiments, polymer preparations provided in accordance with the present invention are prepared according to synthetic methods of Scheme 2 as set forth below:

Scheme 2: Synthetic Route to Polymer Comprising Monomer of Formula (I)

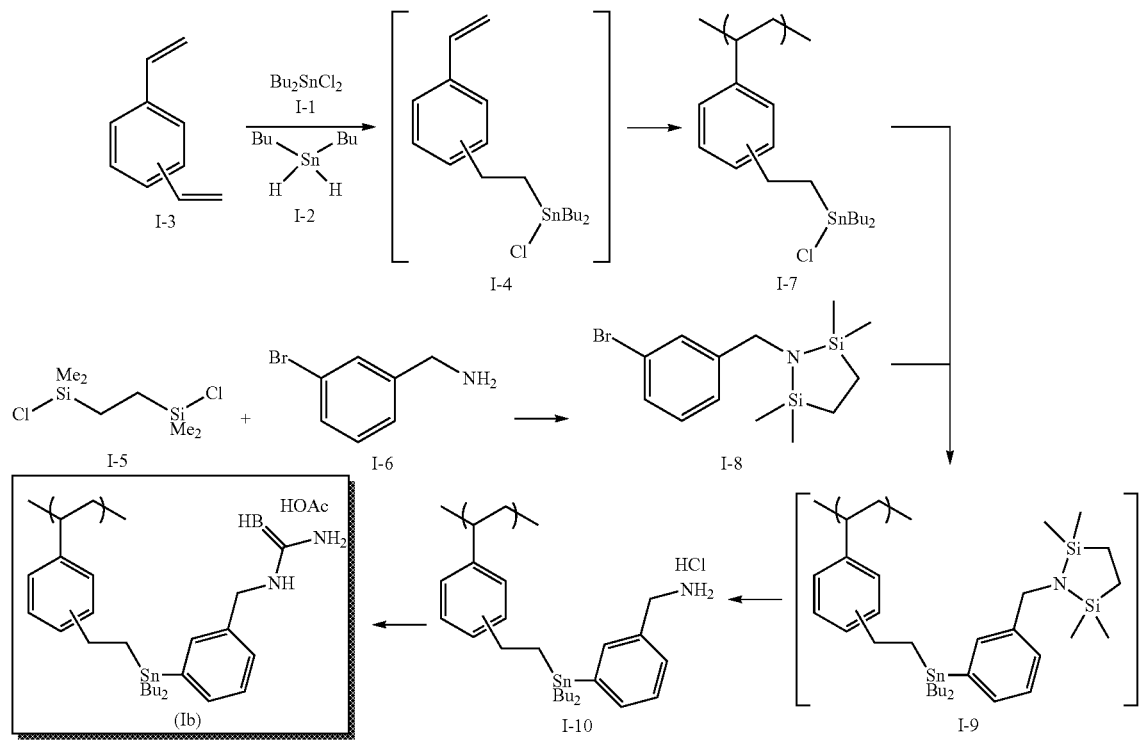

In some embodiments, provided polymer preparations are prepared as follows. Di-n-butyltin dichloride starting material is reduced using hydride. As described below in Examples 1a and 1b, Applicants discovered that reduction via NaBH$_4$ was quicker, more robust and higher yielding than previously-described reactions, which typically utilized LiAlH$_4$. Reduction with NaBH$_4$ was safer and more amenable to scale-up. In some embodiments, temperature is maintained between 0° C. and 10° C. Applicants found that the resulting di-n-butyltin dihydride was easier to purify upon work-up from reduction with NaBH$_4$ than it was upon reduction with LiAlH$_4$. Without being bound by theory, it is believed that freshly prepared di-n-butyltin dihydride, upon reduction with NaBH$_4$, generates cleaner tin-containing starting material and contributes, ultimately, to a cleaner form of polymer with fewer leachable tin-containing fragments. In some embodiments, aqueous work-up of the reduction with NaBH$_4$ is followed by a distillative purification of the crude di-n-butyltin dihydride.

In some embodiments, 2, 3-bromobenzylamine I-6 freebase is then reacted with 1,2-bis(chlorodimethylsilyl) ethane I-5 in dichloromethane with triethylamine at ambient temperature for at least about 14 hours. In some embodiments, the resultant suspension is filtered, the product containing filtrate concentrated and triturated with hexane to precipitate by-products that are filtered and concentrated to a crude oil. Purification via high vacuum distillation gives the product I-8 as colorless oil.

In the following step, di-n-butyltin dihydride I-2 is combined with di-n-butyltin dichloride I-1 in the presence of silica purified divinyl benzene and AIBN at ambient temperature to form the 3,4-(2-dibutylchlorostannyl ethyl) vinyl benzene monomer I-4. This monomer undergoes suspension polymerization in aqueous 1-octanol at reflux with additional silica purified divinyl benzene and AIBN to form polymer I-7, which is isolated by filtration and washed with water, prior to centrifugal washing with one or more solvents, including acetone, methanol, toluene and tetrahydrofuran.

The next step involves an initial reaction of I-8 in tetrahydrofuran at −65 to −80° C. with 2.5M n-butyl lithium in hexane. Polymer I-7 is then charged in a single portion and reaction continues at −65 to −80° C. for 12-18 hours. The suspension is warmed to room temperature, quenched with methanol and acid, such as 1M aqueous HCl, is used to adjust the pH to 4 to 5 for removal of the silyl protecting group. Following overnight agitation at ambient temperature, polymer I-10 is then collected by centrifugation and washed with methanol, methanol/water (1:1), and finally methanol.

Next, polymer I-10 is coupled with cyanamide and triethylamine in toluene at 54-56° C. for about 24 to 26 hours to form the guanidinium chloride intermediate polymer (Ia). This is isolated and washed centrifugally with acetonitrile, methanol and acetonitrile again prior to drying in vacuo. An acetate salt swap is then performed via multiple (e.g., 8) centrifugal washes using 1.0M sodium acetate in 70:30 ethanol:purified water to form the guanidinium acetate polymer (Ib).

The resultant acetate salt of the polymer comprising monomer of formula (I) is subjected to a multi-step purification protocol. First, the resulting polymer (Ib) acetic acid salt is washed with 95% aqueous ethanol (8×4.3 vol.) then isolated by filtration under nitrogen using a Buchner flask and funnel. Polymer (Ib) is dried in a vacuum at ambient temperature. Second, the vacuum is stopped and the Buchner funnel, containing polymer (Ib), is charged with nitrogen gas and absolute ethanol (4×4.30 vol). The absolute ethanol washes under nitrogen further purify polymer (Ib) and remove traces of water from the wet-cake. Third, polymer (Ib) is subjected to a multi-stage drying process encompassing (i) drying at ambient temperature and pressure with a flow of nitrogen, (ii) drying at ambient temperature under vacuum with a flow of nitrogen, and (iii) drying at 30° C. to 40° C. under vacuum with a flow of nitrogen to drive off residual solvent. Polymer (Ib) is sensitive to excessive heat but tolerates gently heating of this multi-stage drying process. Finally, purified polymer (Ib) is stored under an inert gas, such as nitrogen and, in some instances, cooled to −20° C. for storage until use.

In some embodiments, the present disclosure provides and/or utilizes a multi-step purification protocol, including aqueous ethanol washes, anhydrous ethanol washes, vacuum, heating and storage under nitrogen gas at reduced pressure was found to greatly improve the purity and stability of the polymer comprising monomer of formula (I), such that leachable tin is minimized to a level of 0 ppm to 150 ppm.

According to some aspects, provided are methods for preparing a purified composition of a polymer comprising monomer of formula (I):

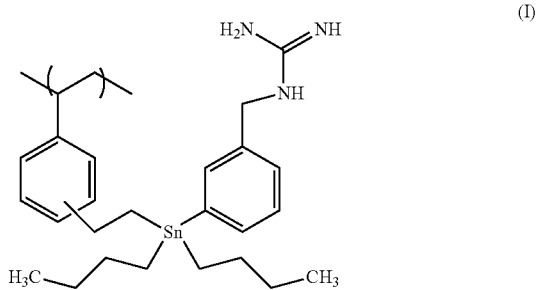

or a pharmaceutically acceptable salt thereof, the method comprising the steps of:
  solvent-treating a preparation comprising the polymer or pharmaceutically acceptable salt thereof, by contacting the preparation with a solvent, and then removing substantially all of the solvent so that a solvent-depleted material comprising the polymer or pharmaceutically acceptable salt thereof is generated; and
  subjecting the solvent-depleted material to vacuum, and to a temperature within a range of about 30° C. to about 50° C.,
  the subjecting being performed under conditions and for a time sufficient so that not more than about 150 ppm of leachable tin is present and, therefore, a purified composition of the polymer, or pharmaceutically acceptable salt thereof, has been produced.

In some embodiments, the preparation is heated under an inert gas, such as argon or nitrogen. In some embodiments, the solvent-depleted material is protected from moisture and/or $O_2$ and stored at ambient or reduced temperature (e.g., below 10° C., 0° C., −10° C., −20° C., or −30° C.).

In some embodiments, the present invention utilizes a solvent that is or comprises methanol, ethanol, diethyl ether, tetrahydrofuran, dichloromethane, hexane, acetone, toluene, acetonitrile, or combinations thereof. In some embodiments, the present invention utilizes a solvent that is an alcohol, for example, methanol or ethanol. In some embodiments, the present invention utilizes a solvent that is or comprises ethanol.

Applicants have found it beneficial, in some instances, to run multiple (e.g., 2-15) "wash cycles," where each wash cycle includes the steps of solvent-treating a preparation comprising the polymer or pharmaceutically acceptable salt thereof and removing substantially all of the solvent. In some embodiments, 2-5 wash cycles are used whereby the preparation is solvent-treated, and then the solvent is substantially removed, 2-5 times. In some embodiments, 5-10 cycles are used whereby the preparation is solvent-treated, and then the solvent is substantially removed, 5-10 times. In some embodiments, 10-15, or more wash cycles are used whereby the preparation is solvent-treated, and then the solvent is substantially removed, 10-15 or more times. In some embodiments, the preparation is further subjected to one cycle of heat at 30° C. to 50° C. and/or vacuum. In some embodiments, the preparation is further subjected to 1-10 cycles of heat at 30° C. to 50° C. and/or vacuum.

Without being bound by theory, Applicants found that aqueous solvents effectively removed salts and water-soluble contaminants from the polymer comprising monomer of formula (I), whereas anhydrous solvents, such as absolute ethanol, effectively removed water from the polymer preparations. Applicants found it beneficial, in some instances, to contact a preparation with an aqueous solvent, remove the aqueous solvent, and further contact the preparation with an anhydrous solvent, and likewise remove the anhydrous solvent from the polymer. For example, in some embodiments, the polymer or salt thereof, is contacted with aqueous ethanol, the aqueous ethanol is substantially removed, the preparation is further contacted with anhydrous ethanol, and the anhydrous ethanol is likewise removed from the polymer.

In some embodiments, the step of solvent-treating the preparation comprises first and second solvent-treating steps, performed with first and second solvents, wherein the first solvent is a water miscible solvent, such as methanol, ethanol, or diethyl ether, and the second solvent is an anhydrous water miscible solvent. In some embodiments, the first solvent is aqueous methanol, ethanol, or diethyl ether, and the second solvent is anhydrous methanol, ethanol, or diethyl ether.

Applicants developed polymer preparations, according to the present methods, that generally contain lower levels of water than polymer preparations prepared according to methods described in U.S. Pat. No. 7,658,910. Without being bound by theory, it is believed that reduced levels of water in the presently disclosed polymer preparations contribute to the robust stability and low levels of leachable tin-containing impurities, relative to those of polymer preparations prepared according to methods described in U.S. Pat. No. 7,658,910.

In some embodiments, the resulting polymer preparations contain water at a level of less than 2.0 wt % water, e.g., relative to the wt % of polymer in the preparation. In some embodiments, the polymer preparations contain less than 1.5 wt % water, less than about 1.4 wt % water, less than about 1.3 wt % water, less than about 1.2 wt % water, less than about 1.1 wt % water, less than about 1.0 wt % water, less than about 0.9 wt % water, less than about 0.8 wt % water, less than about 0.7 wt % water, less than about 0.6 wt % water, less than about 0.5 wt % water, less than about 0.4 wt % water, less than about 0.3 wt % water, less than about 0.2 wt % water, or less than about 0.1 wt % water, or less than about 0.05 wt % water, e.g., relative to the wt % of polymer in the preparation.

In some embodiments, the preparation is heated at 25° C. to 80° C. In other embodiments, the preparation is heated at 30° C. to 60° C. In some embodiments, the preparation is heated at 30° C. to 50° C. In some embodiments, the preparation is heated at 30° C. to 40° C.

In some embodiments, the preparation is heated at any of the above-indicated temperature ranges for 5-60 minutes. In some embodiments, the preparation is heated at any of the above-indicated temperature ranges for 1-4 hours. In some embodiments, the preparation is heated at any of the above-indicated temperature ranges for 4-12 hours. In some embodiments, the preparation is heated at any of the above-indicated temperature ranges for 12-24 hours. In some embodiments, the preparation is heated at any of the above-indicated temperature ranges for 1-2 days. In some embodiments, the preparation is heated at any of the above-indicated temperature ranges for 2-6 days. In some embodiments, the preparation is heated at any of the above-indicated temperature ranges for 1-2 weeks.

In some embodiments, the preparation is subjected to a vacuum for 1-12 hours. In some embodiments, the preparation is subjected to a vacuum for 12-24 hours. In some embodiments, the preparation is subjected to a vacuum for 1-2 days. In some embodiments, the preparation is subjected to a vacuum for 2-6 days. In some embodiments, the preparation is subjected to a vacuum for 1-2 weeks.

According to some aspects, provided are methods for preparing meta-iodobenzylguanidine (MIBG):

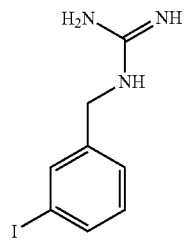 [SMILES: N=C(N)NCc1cccc(I)c1]

or a pharmaceutically acceptable salt thereof, comprising contacting an iodide salt with preparation comprising a polymer comprising monomer of formula (I):

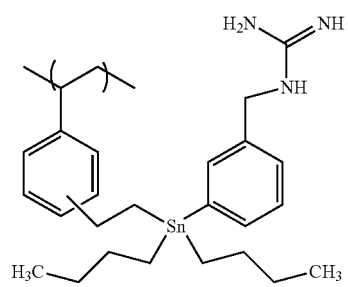

(I)

or a pharmaceutically acceptable salt thereof, the preparation comprising leachable tin at a level of 0 ppm to 150 ppm.

In some embodiments, the method comprises any one of the preparations comprising the polymer comprising monomer of formula (I) described above.

In some embodiments, the method yields MIBG, or a pharmaceutical composition comprising MIBG, the pharmaceutical composition comprising leachable tin at a level of 0 ppm to 150 ppm.

Methods of Administration

In some aspects, provided is a method, the method comprising administering to a subject a pharmaceutical composition comprising:

(a) meta-iodobenzylguanidine (MIBG):

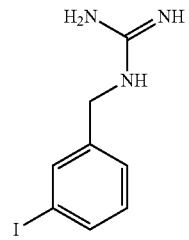

or a pharmaceutically acceptable salt thereof, wherein MIBG is formed by contacting an iodide salt with a preparation of a polymer comprising monomer of formula (I):

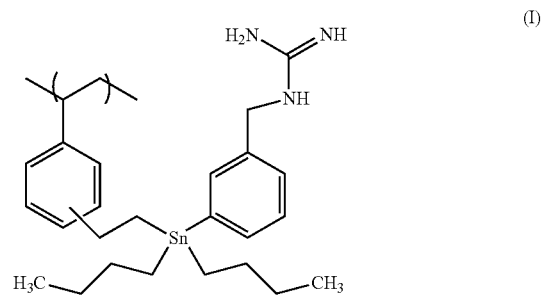

(I)

or a pharmaceutically acceptable salt thereof, the preparation of the polymer comprising monomer of formula (I) comprising leachable tin at a level of 0 ppm to 150 ppm;

(b) a pharmaceutically acceptable carrier, adjuvant, or vehicle.

According to further aspects, provided is a method, the method comprising administering to a subject a pharmaceutical composition comprising the compound of formula (VI):

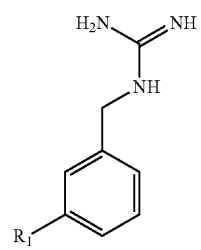

(VI)

or a pharmaceutically acceptable salt thereof, and a pharmaceutically acceptable carrier, adjuvant, or vehicle, wherein $R_1$ is a radioisotopic label, and the pharmaceutical composition comprises leachable tin at a level of 0 ppm to 150 ppm.

In some embodiments, the method comprises administering to a subject a pharmaceutical composition comprising meta-iodobenzylguanidine (MIBG):

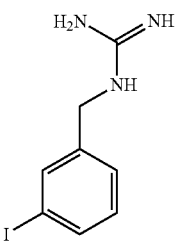 [SMILES: N=C(N)NCc1cccc(I)c1]

or a pharmaceutically acceptable salt thereof, and a pharmaceutically acceptable carrier, adjuvant, or vehicle, wherein the pharmaceutical composition comprises leachable tin at a level of 0 ppm to 150 ppm.

In some embodiments of the method, the pharmaceutical composition, comprising MIBG, or the compound of formula (VI) or a pharmaceutically acceptable salt thereof, has leachable tin at a level below about 150 ppm, 140 ppm, 130 ppm, 120 ppm, 110 ppm, 100 ppm, 90 ppm, 80 ppm, 70 ppm, 60 ppm, 50 ppm, 40 ppm, 30 ppm, 20 ppm, 10 ppm or 5 ppm.

In some embodiments of the method, the pharmaceutical composition has leachable tin at a level within a range of about 0 ppm to about 100 ppm upon administration. In some embodiments of the method, the pharmaceutical composition has leachable tin at a level within a range of about 0 ppm to about 75 ppm upon administration. In some embodiments of the method, the pharmaceutical composition has leachable tin at a level within a range of about 0 ppm to about 50 ppm upon administration. In some embodiments of the method, the pharmaceutical composition has leachable tin at a level within a range of about 0 ppm to about 25 ppm upon administration. In some embodiments of the method, the pharmaceutical composition has leachable tin at a level within a range of about 0 ppm to about 10 ppm upon administration. As used herein, the term "upon administration" refers to a period of time at or just prior to administration, for example, on the day prior to administration, on the same day as administration, within eight hours of administration, with two hours of administration, within one hour of administration, or at the same time as administration to the subject.

In some embodiments of the method, the preparation of a polymer is any of the preparations described herein.

In some embodiments of the method, the iodide salt is sodium I-131 iodide.

In some embodiments of the method, the subject is in need of imaging for one or more potential neuroendocrine tumors in the subject. In some embodiments of the method, the subject is in need of treatment for one or more neuroendocrine tumors in the subject. In some embodiments of the method, the neuroendocrine tumors are metastatic. In some embodiments of the method, at least one or more neuroendocrine tumors are located within the adrenal glands of the subject. In some embodiments of the method, the subject is in need of treatment for one or more pheochromocytomas. In some embodiments of the method, the subject is in need of treatment for one or more paragangliomas, i.e., outside the adrenal glands of the subject. In some embodiments of the method, the subject is in need of treatment for one or more neuroblastomas.

EXEMPLIFICATION

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using the same or similar procedures.

Scheme 3

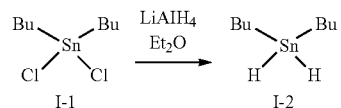

Example 1a: Synthesis of Di-n-butyltin dihydride I-2, via LiAlH$_4$

Di-n-butyltin dichloride (25.0 g, 1.0 eq) was dissolved in diethyl ether (1.65 vol) at ambient temperature to form a solution. Separately, a solution of 1M lithium aluminum hydride in diethyl ether solution (1.0 eq) and diethyl ether (2.48 vol) was prepared and added at ≤23° C. over 60 minutes, with subsequent reflux at 34-35° C. for 17 hours 40 minutes. Hydroquinone (0.023 eq) was then charged and the reaction slowly quenched via the drop-wise addition of purified water at ≤25° C. A solution of potassium sodium tartrate tetrahydrate (0.95 eq) in purified water (3.31 vol) was prepared and charged to the suspension at ambient temperature, with subsequent agitation for 1 hour at 23° C. A grey bi-phasic "sludge" was formed with large clumps of by-products present. TLC analysis indicated the reaction was complete (90:10 cyclohexane:ethyl acetate eluent). Diethyl ether extractions of the aqueous sludge were problematic, with poor phase separation and blockages of the outlet valve during discharge from the vessel. After drying over magnesium sulphate, washing and concentration, 17.4 g (90% yield) of crude di-n-butyltin dihydride was obtained. This was purified via high vacuum distillation. Di-n-butyltin dihydride was collected at 5-12 mbar between ~56-74° C. as colorless oil in ~65% yield. It was found that this reaction was not robust, and would be challenging to scale-up, mainly due to the difficult work-up.

Scheme 4

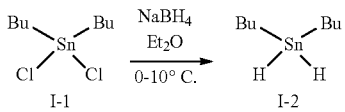

Example 1b: Synthesis of Di-n-butyltin dihydride I-2, via NaBH$_4$

The following reduction with NaBH$_4$ was adapted from methods described by A. G. Hernan et al., *Journal of Organometallic Chemistry*, 691, (2006), pp 1466-1475.

Small-scale: Sodium borohydride (5.33 eq) was dissolved in purified water (11.3 vol) at 0° C. and deoxygenated by bubbling nitrogen for 30 minutes. A solution of di-n-butyltin dichloride (9.0 g, 1.0 eq) was prepared in 11.3 vol of diethyl ether and added slowly over a period of 45 minutes, with the solution then stirred for a further 15 minutes once addition was complete. The product containing organic layer was the separated, washed with purified water (2×2.78 vol), dried over magnesium sulphate, filtered and concentrated under vacuum to give di-n-butyltin dihydride as a colorless oil (6 g, 85% yield). $^1$H NMR confirmed the di-n-butyltin dihydride was formed. To ensure high purity di-n-butyltin dihydride was produced, distillative purification was added.

Large Scale: The sodium borohydride-based reduction was successfully scaled to 90 g. The reduction was again complete by TLC after 20 minutes and work-up proceeded to give 67.6 g (97% yield) of crude di-n-butyltin dihydride. This underwent distillative purification from a 1.0 L RBF with Vigreux column. No foaming was observed and 53.5 g (77% yield) of dihydride was collected as a clear colorless liquid between 5-6 mbar at 56° C. $^1$H and $^{13}$C NMR confirmed di-n-butyltin dihydride had been collected. GC analysis indicated a purity of >99% area. Although the lower aqueous phase during the washing step was still a suspension it was much less problematic to separate from the upper product containing diethyl ether phase, relative to the corresponding reaction with LiAlH$_4$. This reduction via NaBH$_4$ was quicker, more robust and higher yielding than the corresponding reaction with LiAlH$_4$.

was filtered to remove by-products, the wet-cake washed with dichloromethane (2×1.54 vol) and concentrated to a crude oil at 35-40° C. in vacuo. The crude product was triturated with hexane (6.2 vol) to further precipitate by-products, filtered and the wet-cake washed with hexane (2×1.54 vol). The filtrate was again concentrated to a crude oil at 40-45° C. in vacuo. Distillation purification was used to isolate 1-(3-bromobenzyl)-2,2,5,5-tetramethyl-1,2,5-azadisololidine which was collected between 150-160° C. between 5-10 mbar as a colorless oil in ~62% yield.

Scheme 5

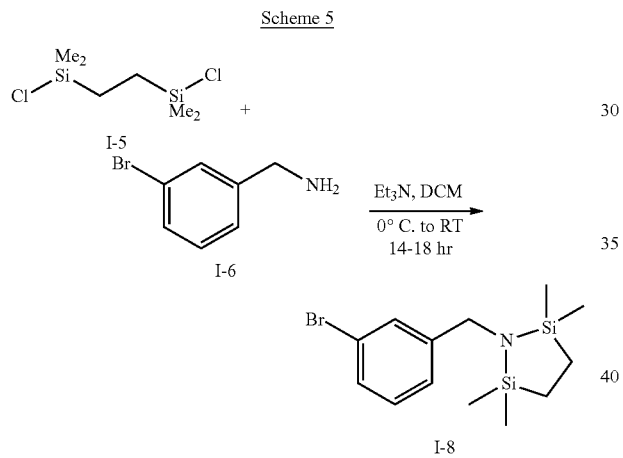

Scheme 6

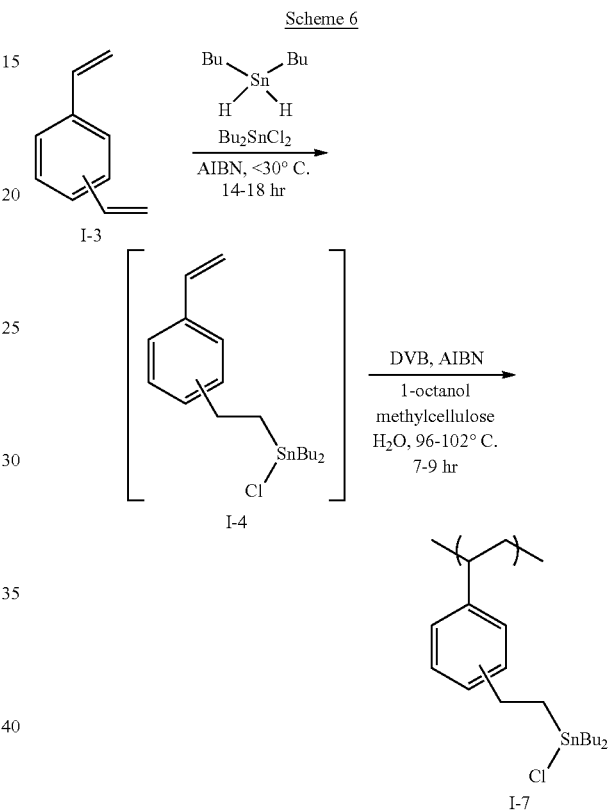

Example 2: Synthesis of 1-(3-Bromobenzyl)-2,2,5,5-tetramethyl-1,2,5-azadisololidine, I-8

Free-Basing: 3-Bromobenzylamine hydrochloride (1.0 eq) was dissolved in purified water (15.8 vol) at ambient temperature. Separately sodium hydroxide (1.05 eq) was dissolved in purified water (0.83 vol) and added to the above solution at ambient temperature and agitated for 30 minutes. The freebase was extracted using 3×5.0 vol dichloromethane washes, which were dried over magnesium sulphate prior to filtration to remove the drying agent and subsequent rotary concentration to dryness at 35 to 40° C. 3-Bromobenzyl amine freebase was obtained as a yellow/orange oil in ~100% yield.

Reaction: 3-Bromobenzylamine (48.7 g, 1.0 eq) was dissolved in dichloromethane (7.4 vol) and triethylamine (2.75 eq) to form a solution, which was cooled under nitrogen to 0-5° C. Separately a solution of 1,2-bis(chlorodimethylsilyl)ethane (1.0 eq) in dichloromethane (5.13 vol) was prepared and added drop-wise over ~30 min at 0-5° C. The resultant suspension was allowed to warm to ambient and stir for a minimum of 14 hours after which the reaction

Example 3: Synthesis of Polymer Comprising Monomer I-7

3,4-Divinylbenzene was purified using a silica gel column to remove radical scavengers prior to usage in this process. Di-n-butyltin dichloride (0.97 eq) was dissolved in filtered divinylbenzene (1.23 eq) at ambient temperature then cooled to <10° C. Di-n-butyltin dihydride (1.0 eq) was then charged to the reaction mixture followed by filtered divinylbenzene (1.18 eq) and AIBN (0.040 eq). Cooling was removed and the solution agitated at <30° C. for 14 to 18 hours to form the monomer I-4.

To this was then charged a solution of methylcellulose (15 cPs, 0.023 w/w) in purified water (8.94 vol) at ambient temperature followed by filtered divinylbenzene (0.55 eq), 1-octanol (3.7 vol) and AIBN (0.065 eq). The resultant suspension was heated to reflux at (~98-102° C.) at ~500 rpm and agitated for 7-9 hours to form polymer comprising monomer I-7. Heating was removed and the mixture agitated for at least 14 hours prior to the addition of purified water (9.6 vol).

Polymer comprising monomer I-7 was collected by filtration and re-slurried a further five times with purified water (each 9.6 vol) with isolation by filtration. This was followed by the following re-slurries, each of which is isolated by centrifugation: Acetone (5×7.7 vol); Methanol (2×7.7 vol); Toluene (3×7.7 vol); and THF (2×7.7 vol).

Polymer comprising monomer I-7 was then dried in vacuo to constant weight (<1% loss on drying over 1 hour minimum) at ambient temperature. Yield 56%.

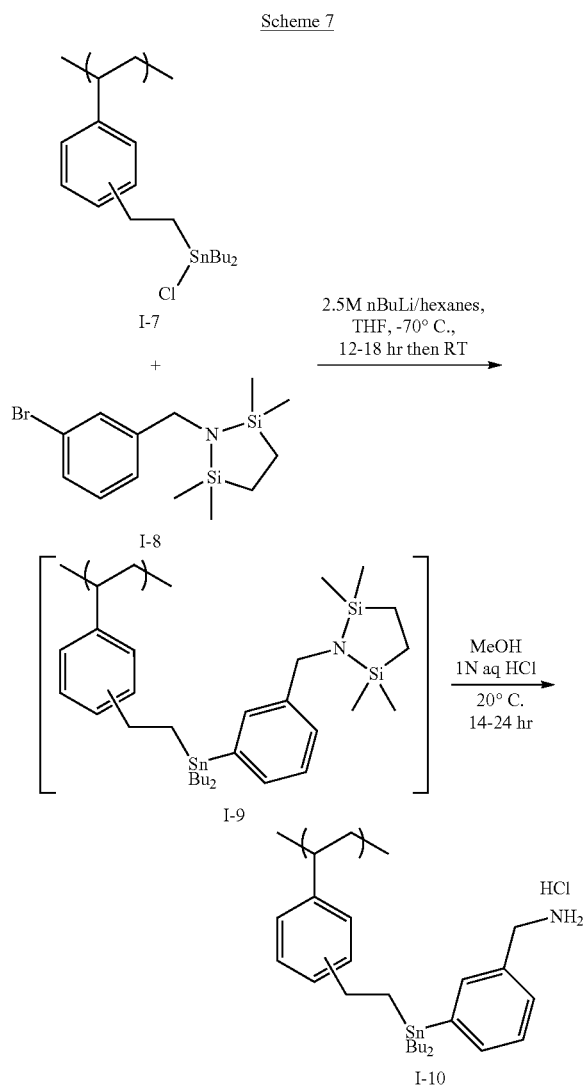

Example 4: Synthesis of Polymer Comprising Monomer I-10

1-(3-Bromobenzyl)2,2,5,5-tetramethyl-1,2,5-azadisilolidine (1.06 eq.) was charged to a flask followed by tetrahydrofuran (8.75 vol.) and the solution cooled to <−65° C. 2.5M n-butyl lithium in hexane (1.06 eq.) was added over 30 minutes. Polymer comprising monomer I-7 was added in a single dry portion after which the reaction mixture is stirred at <−65° C. for 7-9 hours then allowed to warm to room temperature for 1-2 hours. Methanol was added followed by 1M HCl (aq.) to adjust the pH to 4-5. The polymer comprising monomer I-10 was then collected by centrifugation.

The liquid was decanted and polymer comprising monomer I-10 washed sequentially with methanol (4×6.25 vol.), methanol/water (1:1) (2×6.25 vol.), methanol (4×6.25 vol.) and then dried in a vacuum oven giving polymer comprising monomer I-10 in a yield of 82%.

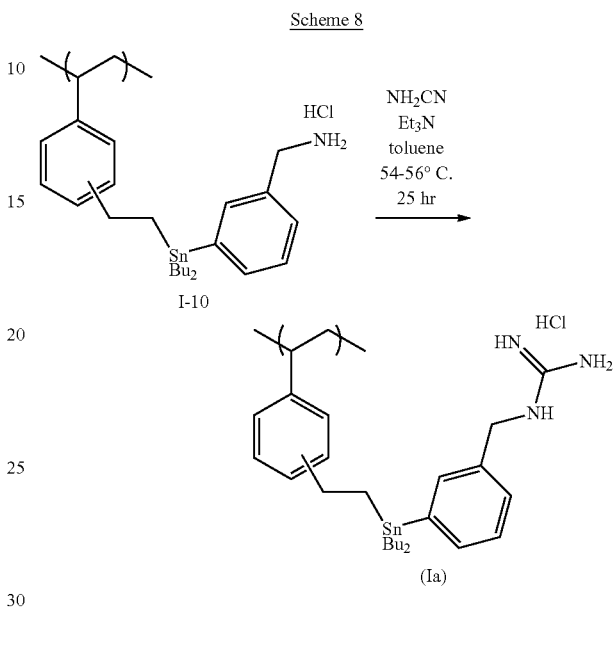

Example 5: Guanidinylation of Polymer Comprising Monomer I-10 to Form Polymer Comprising Monomer (Ia) HCl Toluene (8.6 vol.) was charged to a flask and heated to 54-56° C. Polymer comprising monomer I-10 (1.0 eq.) was added, followed by cyanamide (9.13 eq.) and triethylamine (0.018 eq.). The reaction mixture was stirred at 54-56° C. for 24-26 hours then cooled to ambient temperature. Polymer comprising monomer (Ib) was isolated by centrifugation and washed sequentially with acetonitrile (4×4.7 vol), methanol (4×4.7 vol.) and acetonitrile (2×4.7 vol.). The isolated polymer was dried in a vacuum oven at ambient temperature.

Applicants identified cyanamide coupling reaction time (24 to 26 hours) and temperature (54-56° C.) as critical parameters for controlling impurity formation, particularly mIBBG. A 10 g trial of this reaction was performed to monitor impurity formation between ~20 to 48 hours during cyanamide coupling at 54 to 56° C. At each time point analyzed, ~2.5 ml of the suspension was removed, filtered and washed with 5×5 mL of methanol prior to vacuum drying at ambient temperature.

The results of these experiments showed a gradual decrease in mIBA starting material from 0.35% at 19.5 hours to 0.09% after 48 hours. The mIBBG impurity gradually increased to 1.02%, but only after 48 hrs. Within a 15 to 30, 18 to 28, or more particularly 24-26 hour reaction time window, the reaction appears to give a good balance between low residual mIBA, whilst not elevating mIBBG formation.

The above-described impurity time point formation experiments suggest that the process, in some embodiments, should be operated within the supplied process parameters of e.g., 50-60° C. for 15 to 30 hours, 52-58° C. for 20 to 28 hours, or, more particularly, 54-56° C. for 24 to 26 hours.

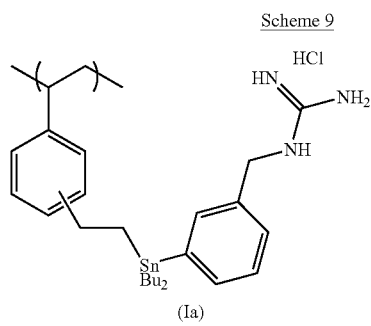

Scheme 9

(Ia)

(Ib)

Example 6: Counter Ion Exchange of Polymer Comprising Monomer (Ia) HCl to Form and Purify Polymer Comprising Monomer (Ib) HOAc Step 1: Counter ion exchange of polymer comprising monomer (Ia) hydrochloride salt was achieved by slurrying in 1M sodium acetate in 70% aqueous ethanol, followed by and centrifugation (9×4.3 vol.).

Step 2: The resulting polymer comprising monomer (Ib) HOAc salt was purified by washing with 95% aqueous ethanol (8×4.3 vol.) then isolated by filtration under nitrogen using an appropriate clean, dry Buchner flask and funnel. Polymer comprising monomer (Ib) (84% yield) was dried in a vacuum oven at ambient temperature.

Step 3: Vacuum was stopped and the Buchner funnel containing polymer comprising monomer (Ib) was charged with absolute ethanol (4×4.30 vol) under nitrogen gas. The absolute ethanol washes, under nitrogen, were found to further purify polymer comprising monomer (Ib) and remove traces of water from the wet-cake.

Example 7: Analytical Methods for Determination of Leachable Tin Levels by ICP-MS Concentrations of leachable tin in polymer comprising monomer (Ib) were determined according to the general analytical methods outlined in the Tables below.

TABLE 1

Instruments, Equipment, Materials and Reagents

| | | Description |
|---|---|---|
| Instruments | ICP-MS | Agilent 7900 |
| | Balance | Minimum 5 place balance |
| | Pestle and Mortar | |
| | Flask Shaker | Stuart Scientific |
| Equipment | Plasticware | Various sizes of volumetric flasks and measuring cylinders |
| | Plastic centrifuge tubes | 50 ml, 15 ml, and 10 ml tubes of suitable grade with volume markings |
| | Auto pipettes | Varying capacity from 50 µl to 5000 µl |
| | Plastic pipettes | 500 ml volumetric |
| | Syringes | 10 ml |
| | Syringe filters | PTFE Acrodisc 0.2 gm |
| Materials | Indium (In) Standard | |
| | Tin (Sn) Standard | |
| | Cerium (Ce) Standard | |
| | Cobalt (Co) Standard | |
| | Yttrium (Y) Standard | |
| | Tuning solution | |
| Reagents | Water | UHQ Grade |
| | Ethanol | Absolute |
| | NitricAcid(67-70%) | ICP-MS grade |
| | Hydrochloric Acid 20% | ICP-MS Grade |

TABLE 2

Preparation of Reagents

| Reagent | Description | Storage | Expiry |
|---|---|---|---|
| Diluent A | 5% Ethanol 25 ml Absolute Ethanol diluted to 500 ml in volumetric flask | Ambient | 1 month |
| Diluent B | 2% Nitric Acid 29.4 mL Concentrated Nitric acid made up to ILin a volumetric flask | Ambient | 1 month |

TABLE 3

Internal Standard Preparation

| Solution | Replicates | Add | Make to Volume (mL) | With Diluent | Storage | Expiry |
|---|---|---|---|---|---|---|
| 2 ppm in Internal standard | 1 | 5.0 ml of 10 ppm In Internal standard | 25 ml | B | Ambient | 10 days |
| 2 ppm Sn Standard | 1 | 1.0 ml of 100 ppm Sn Standard | 50 | B | Ambient | 10 days |
| 2 ppm Sn Check Standard | 1 | 1.0 ml of 100 ppm Sn Standard | 50 | B | Ambient | 10 days |

TABLE 4

Working Standard Preparation

| Solution | Add | Make to volume (ml) | With Diluent | Storage | Expiry |
|---|---|---|---|---|---|
| Calibration Blank | 1 ml concentrated nitric acid + 2.5 ml ethanol and 0.5 ml internal standard | 50 ml in plastic centrifuge tube. | UHQ water | ambient | 10 days |
| 50 ppb working standard | 2.5 ml of 2 ppm Sn Standard + 5.0 ml Ethanol + 1.0 ml of Internal Standard + 2.0 ml conc. Nitric acic | 100 ml | UHQ water | Ambient | 10 days |
| 150 ppb working standard | 7.5 ml of 2 ppm Tin Standard + 5.0 ml Ethanol + 1 ml of Internal Standard + 2.0 ml conc. Nitric acid | 100 ml | UHQ water | Ambient | 10 days |
| 50 ppb check standard | 2.5 ml of 2 ppm Sn check Standard + 5.0 ml Ethanol + 2.0 ml conc. Nitric acid | 100 ml | UHQ water | Ambient | 10 Days |

Sample Preparation Steps:

1. Using a pestle and mortar, grind enough drug to weigh the below to a fine powder.
2. In a clean Teflon 50 ml centrifuge tube, accurately weigh approximately 40 mg of drug material.
3. Add 10.0 ml of 5% ethanol.
4. Shake on low for 1 hour.
5. Filter through 0.45 μm PTFE filters into a HDPE bottle. Add 1 drop of 2% nitric acid to the sample.
6. Prepare a Method blank with the samples by proceeding through the above steps using UHQ water in place of the sample. Prepare the method blank and the samples in singular. Store at ambient with an expiry date of 6 days.

TABLE 5

Instrument Parameters'. The ICP-MS instrument is to be set up with the following parameters as an example:

| Parameter | Setting |
|---|---|
| Forward Power | (7500c) 1500, (7500a) 1300 |
| Acquire Integration Time | 0.10 sec Sn and 0.05 sec In per point |
| Integration Mode | Auto |
| Replicates | 3 |
| Points per peak | 3 |
| Validated masses | $^{118}Sn$, $^{120}Sn$ |
| Preferred Mass | $^{118}Sn$ |
| Internal Standard Mass | $^{115}In$ |
| Rinse Time | 100 sec (may be increased if needed) |
| Rinse rate | 0.5 rps |
| Rinse Solution | 1% $HNO_3$ and HCl |
| Uptake time | 40 sec (may be increased if needed) |
| Uptake rate | 0.5 rps |
| Stabilization Time | 20 sec |
| Analysis Pump Rate | 0.1 rps |
| Spray Chamber | Quartz Double Pass |
| Nebulizer | Concentric |
| Nebulizer Flow rate | 0.95 to 1.16 L/min |
| All other settings | Determined by Tune |

TABLE 6

Tuning Requirements

| Parameter | Setting |
|---|---|
| Tuning Masses | $^{59}Co$, $^{89}Y$, $^{140}Ce$ |
| Resolution @ $^{59}Co$, $^{89}Y$, $^{140}Ce$ | ± 0.10 AMU, W-10% 0.65 to 0.80 |
| Minimum CPS $^{89}Y$, $^{140}Ce$ | 200,000 (20,000 Counts/0.1 sec) |
| $^{89}Y$, $^{140}Ce$ % RSD | ≤10% |
| Oxide 156/140 AMU | ≤2% |
| Double Charged 70/140 AMU | ≤5% |

TABLE 7

Interference Equations

| Affected Isotope | Correction |
|---|---|
| $^{120}Sn$ | 120*1 − 125*0.01344726 |
| $^{115}In$ | 115*1 − 118*0.01403799 |

TABLE 8

Isotope LOQ's

| Isotope | LOQ (μg/L) |
|---|---|
| $^{118}Sn$ | 0.3 |
| $^{120}Sn$ | 0.3 |

Method Procedure

1. Set up the ICP-MS according to the parameters listed in (Tables 5-7) and Instrument SOP.
2. Perform a tune using the tuning solution. Tune the ICP-MS to obtain the desired resolution, sensitivity, oxide ratio and doubly charged ratios as specified in Table 6. Perform a P/A factor using the 150 ppm Tin Standard.
3. Prepare the standards and sample solutions as per above sections and the Sample Preparation Steps.
4. Add 754, if Indium internal standard to 7.5 ml of filtered sample and mix. Load the samples and standards in the auto-sampler.
5. Calibrate the instrument with the calibration blank and the 50 ppm standard.
6. Run the blank as a sample after the calibration is complete. The blank must read less than the LOQ (Table 8). If the blank is out of specification, investigate the cause and correct the problem before continuing with the analysis.

7. Run the calibration check standard as a sample after the blank is run. The check standard must read 50 ppm±5 ppm, and the RSD between the 3 replicate instrument readings must be less than 4%. If the check standard is out of specification, investigate the cause and correct the problem before continuing with the analysis.
8. Analyze the method blank. It is best if the method blank reads less than the LOQ (Table 8). If the method blank is above these values, but the element concentration in the sample is greater than 10 times the method blank level or less than the LOQ, the samples can be run as prepared. If the element concentration in the samples is less than 10 times the method blank level, but above the LOQ, re-prepare both the blank and the samples. Take any necessary steps to achieve a clean blank.
9. Analyze the samples. Samples may be diluted further as needed to bring within the linear range. The upper limit of the linear range verified during validation is 5000 µg/L. Maintain acid strength on all dilutions and total internal standard concentration of 20 µg/L indium in all dilutions.
10. Analyze the 50 ppm calibration standard and the blank after every 10 samples, or at the end of the samples, whichever comes first. Do not run more than 10 samples before running the 50 ppm standard and a blank. The 50 ppm standard must read 50 ppm±5 ppm, the RSD between the 3 replicates instrument readings must be <4% and the blank must read less than the LOQ. If the 50 ppm standard or the blank is out of specification, the instrument must be recalibrated and all samples analyzed from the time of the last acceptable standard and the blank must be rerun.
11. Analyze the 50 ppm standard and the blank at the end of the analysis. The 50 ppm standard must read 50 ppm±5 ppm, the RSD between the 3 replicate instrument readings must be <4%, and the blank must read less than the LOQ. If the 50 ppm standard or the blank is out of specification, the instrument must be recalibrated and all samples analyzed from the time of the last acceptable standard and blank must be rerun.
12. Place the instrument in standby mode according to SOP.

TABLE 9

Analysis-Perform the Following Typical Injection Sequence

|  | ICP-MS |
|---|---|
| Wash | X |
| Cal Blank | X |
| Calibration Standards | X |
| Wash | X |
| IQC standard | X |
| Wash | X |
| Samples (including duplicates) | X |
| Spiked sample(s) | X |
| Wash | X |
| Check standard after 10 sample and end of sequence | X |
| Wash | X |

TABLE 10

Calculations $$\frac{\mu g}{g} \text{ sample} = \frac{(C \times D \times V)}{(W)}$$

| C | Concentration of element read from the instrument in µg/L |
|---|---|
| V | Volume of sample preparation, in mL |
| W | Weight of sample used, in mg |
| D | Dilution factor (A dilution of 1 mL to 50 mL final volume would yield a D of 50) |

Conversions for the mass and volume units are incorporated into the above equation. Report data as µg/g of tin in the sample. Concentration can be read from the calibration curve directly. If the sample requires dilution to have an element concentration within the calibration range, the dilution factor must be taken into account when determining the final concentration in the sample.

Example 8: Comparative Analysis of Leachable Tin Level in Samples of Polymer Comprising Monomer (Ib) Compositions Prepared According to Methods Disclosed in U.S. Pat. No. 7,658,910

TABLE 11

Teachable Tin by ICP-MS

| Conditions | Result (Sn) |
|---|---|
| Range at time = 0 | 155-318 ppm<br>Mean (n = 9) =<br>198.3 +/− SD 84.5 ppm |
| Range after three years at −20° C. | 576-660 ppm |
| Range after three years at 25° C., 60% relative humidity | 818-928 ppm |
| Range after three years at 40° C., 75% relative humidity | 847-1207 ppm |

The above analyses shows that leachable tin was present at high levels (e.g., 155-318 ppm) in Polymer (Ib) prepared according to methods disclosed in U.S. Pat. No. 7,658,910. The analysis further shows that levels of leachable tin increased over time due to exposure to moisture, O2 and/or ambient and elevated temperature.

Example 9: Analysis of Leachable Tin Levels from Samples of Polymer Comprising Monomer (Ib) Compositions Prepared According to Methods of Examples 1-6

TABLE 12

Teachable Tin by ICP-MS

| Duration (in months) | Storage Conditions and Result (Sn) GMP lots, unless stated otherwise | | |
|---|---|---|---|
| | −20° C. | 25° C. 60% Relative Humidity | 40° C. 75% Relative Humidity |
| 0 | 18-19 ppm (GMP lot)<br>7.9 ppm (non-GMP lot)<br>Mean (n = 2) = 13 ppm | 19 ppm | 19 ppm |

TABLE 12-continued

Teachable Tin by ICP-MS

| Duration (in months) | Storage Conditions and Result (Sn) GMP lots, unless stated otherwise | | |
|---|---|---|---|
| 1 | 20 ppm | 243 ppm | 582 ppm |
| 3 | 14 ppm | 304 ppm | 636 ppm |
|   | 15 ppm | 327 ppm | 447 ppm |
|   | 12 ppm | 476 ppm |   |

GMP = Good manufacturing practices

The above analyses shows that leachable tin was present at reduced levels (e.g., 7.9-19 ppm), for extensive durations, in Polymer (Ib) prepared according to the present methods of examples 1-6.

Example 10: Analytical Method for Determination of Moisture Content by Oven Coulometric Karl Fischer Titration

TABLE 13

Instruments, Equipment, Materials and Reagents

|   |   | Description |
|---|---|---|
| Instruments | KF Coulometer | With oven sampler |
|   | Balance | Minimum 5 place |
| Equipment | Generating electrode | Cell without diaphragm, Mettler |
|   | Vials, seals & cap | Dried overnight at 75° C. prior to use |
|   | Desiccator |   |
|   | Silica Gel |   |
| Reagents | Anolyte | Karl Fischer Reagent AG-oven (Sigma Aldrich Catalogue No. 34739 or equivalent) |
|   | Gas Type | Nitrogen, flow set to 150-200 mL/min |

TABLE 14

Instrument Parameters

| Parameter | Value |
|---|---|
| Sample Parameters | |
| Type | Mass |
| Minimum (g) | 0.135 |
| Maximum (g) | 0.165 |
| Entry | Before |
| Speed (%) | 40 |
| Mix time (s) | 300 |
| Set Temperature | 160° C. |

TABLE 14-continued

Instrument Parameters

| Parameter | Value |
|---|---|
| Control Parameters | |
| Current (μA) | 2.0 |
| End point (mV) | 100 |
| Gen. speed | Normal |
| Termination Parameters | |
| Max. time (s) | 1200 |
| Drift stop | Rei. |
| Drift (μg/min) | 15 |
| Blank (μg) | Auto |
| Drift | Request |
| Calculation 1 | |
| R1 = | X [%]*f1 |
| F1 = | 1.000 |
| Unit | % |
| Decimal Places | 2 |
| Statistics | Yes |
| Max. srel (%) | 0.000 |
| Calculation 2 | |
| R2 = | X [mg]*f2 |
| F2 = | 1.000 |
| Unit | mg |
| Decimal Places | 3 |
| Statistics | Yes |
| Max. srel (%) | 0.000 |
| Standby | Yes |
| Report | |
| Output | Print. + Comp. |
| Type | GLP |

TABLE 15

Test Vials - Prepare the test vials as described in the table below. Close immediately with a seal and cap.

| Solution | Replicates | Add | Storage | Expiry |
|---|---|---|---|---|
| Drift Vial | 1 | Aluminum insert | Ambient | Use immediately |
| Blank Vial | 1 | N/A | Ambient | Use immediately |
| Sample Vial | 2 | 150 mg (±10%) sample | Ambient | Use immediately |

TABLE 16

Analysis - Perform the following analysis sequence:

|   | Water Determination |
|---|---|
| Blank | X |
| Sample 1 replicate 1 | X |
| Sample 1 replicate 2 | X |
| Sample 2 replicate 1 | X |
| Sample 2 replicate 2 | X |
| . . . up to a maximum of 13 analyses . . . | |

TABLE 17

Calculations

Water Content   Water content is calculated by the instrument according to the following equation:

$$\text{Water Content (\%w/w)} = \frac{\{\text{Water} - [B + (D \times T)]\}}{1000} \times \frac{100}{W_{sample} \times 1000}$$

Where
Water = Water content (μg)
B = Blank (μg)
D = Drift (μg/min)
T = Titration Time (minutes)
$W_{sample}$ = Weight of sample (g)
Ensure that replicate results agree within:
If water content    <0.1%   no limit
                           0.1%-1.0%   agree within 0.2% absolute
                           >1.0%      agree within 0.5% absolute

TABLE 18

Reporting

Water Content   Report the mean of two replicates.
Report results <0.3% w/w as <0.3% w/w.

Record the data on an analytical worksheet/workbook.
Compare the results obtained against the relevant specification limit. If the results obtained are in compliance with the specification limit report the results on the RFA form. If the results fail to meet the specification, initiate an OOS investigation.

Example 11: Moisture Content Analysis for Compositions of Polymer Comprising Monomer (Ib) Prepared According to Methods of Examples 1-6

TABLE 19a

Moisture content

| Test | Specification | Result |
|---|---|---|
| Residual Moisture (Water Content by Karl Fischer) at time = 0 | ≤1.5% | 0.92% (GMP) 1.0% (non-GMP) |

TABLE 19b

Moisture content over various durations

| | Storage Conditions and Results (Residual Moisture i.e., Water Content by Karl Fischer) GMP lots, unless stated otherwise | | |
|---|---|---|---|
| Duration (in months) | −20° C. | 25° C. 60% Relative Humidity | 40° C. 75% Relative Humidity |
| 0 | 0.92% (GMP) 1.0% (non-GMP) | 0.92% | 0.92% |
| 1 | 0.99% | 0.86% | 1.1% |
| 3 | 0.60% | 1.6% | 0.78% |

TABLE 19b-continued

Moisture content over various durations

| | Storage Conditions and Results (Residual Moisture i.e., Water Content by Karl Fischer) GMP lots, unless stated otherwise | | |
|---|---|---|---|
| Duration (in months) | −20° C. | 25° C. 60% Relative Humidity | 40° C. 75% Relative Humidity |
| 6 | 0.80% | 0.71% | 0.89% |
| 9 | 0.67% | 0.89% | |

Example 12: Analytical Method for the Determination of Residual Solvents in Composition of Polymer Comprising Monomer (Ib), Using GC Headspace Analysis

TABLE 20a

Instruments, Equipment, Materials and Reagents (Alternative A)

| | | Description |
|---|---|---|
| Instruments | GC | Gas chromatograph with FID and Headspace Sampler |
| Equipment | Balance | Minimum 5 place balance |
| | Column | RES-SOLV 30 m × 0.53 mm 1.00 μm |
| | Liner | 4 mm ID open tube liner (Agilent 210-3003) |
| | Septa | High temperature - Bleed/Temp optimized (Agilent 5183-4757 or equivalent) |
| | Glassware | Grade A |
| | Headspace vials | 20 mL |
| Materials | ARS5483 | Isopropyl acetate |
| | ARS5496 | Tetrahydrofuran |
| Reagents | DMSO | Analytical Grade |

TABLE 20b

| | | Instruments, Equipment, Materials and Reagents (Alternative B) |
|---|---|---|
| | | Description |
| Instruments | GC | Gas chromatograph with FID and Headspace Sampler |
| | Balance | Minimum 5 place balance |
| Equipment | Column | ZB-624, 60 m × 0.53 mm, 3.00 μm |
| | Liner | 2 mm ID open tube liner (Agilent5181-88-18) |
| | Septa | High temperature - Bleed/Temp optimized (Agilent 5183-4757 or equivalent) |
| | Glassware | Grade A |
| | Headspace vials | 20 mL |
| Materials | ARS5443 | Diethylether |
| | ARS5916 | Dichloromethane |
| | ARS5815 | Triethylamine |
| | ARS5413 | Hexane |
| | ARS5467 | Acetone |
| | ARS5414 | Methanol |
| | ARS5402 | Toluene |
| | ARS5814 | Tetrahydrofuran |
| | ARS5424 | Acetonitrile |
| | ARS5465 | Ethanol |
| | ARS5828 | 1-Octanol |
| Reagents | | Analytical Grade N,N-dimethylacetamide (DMA) |

TABLE 21

| | Preparation of reagents | | |
|---|---|---|---|
| Reagent | Description | Storage | Expiry |
| Blank & Standard/Sample Diluent | DMSO (or N,N-dimethylacetamide (DMA)) Use single bottle for entire analysis | Ambient | 1 month |

TABLE 22a

| Instrument Parameters (Alternative A) | | | |
|---|---|---|---|
| GC Oven Parameters | Value | | |
| Initial temperature | 40° C. | | |
| Initial time | 1.70 minutes | | |
| Total run time | 15.37 minutes | | |
| Temperature ramp | Rate (° C./min) | Final Temperature (° C.) | Final hold time (min) |
| | 6.00 | 90.0 | 0 |
| | 30.00 | 250.0 | 0 |
| Inlet Parameters | Value | | |
| Mode | Split | | |
| Initial Temperature | 220° C. | | |
| Split ratio | 7:1 | | |
| Gas Type | Helium | | |
| Column Parameters | | | |
| Column | RES-SOLV, 30 m × 0.53 mm, 1.0 μm | | |
| Mode | Constant Flow | | |
| Initial flow | 4.9 | | |
| Detector Parameters | Values | | |
| Temperature | 260° C. | | |
| Hydrogen flow | 45 mL/minute | | |
| Air flow | 450 mL/minute | | |
| Mode | Constant makeup flow | | |
| Make up flow (Nitrogen) | 10 mL/minute | | |
| Headspace Parameters | | | |
| Oven Temperature | 130° C. | | |
| Loop Temperature | 140° C. | | |
| Transfer Line Temperature | 150° C. | | |
| GC Cycle | 25 minutes | | |

TABLE 22a-continued

| Instrument Parameters (Alternative A) | |
| --- | --- |
| Vial Equilibration Time | 15 minutes |
| Vial Pressurisation Time | 0.2 minute |
| Loop Fill Time | 0.15 minute |
| Loop Equilibration Time | 0.05 minute |
| Injection Time | 1 minute |
| Agitation | High |

TABLE 22b

| Instrument Parameters (Alternative B) | | | |
| --- | --- | --- | --- |
| GC Oven Parameters | Value | | |
| Initial temperature | 45° C. | | |
| Initial time | 3.0 minutes | | |
| Total run time | 26.0 minutes | | |
| Temperature ramp | Rate (° C./min) | Final Temperature (° C.) | Final hold time (min) |
|  | 10.00 | 255.0 | 2.0 |
| Inlet Parameters | Value | | |
| Mode | Split | | |
| Initial Temperature | 220° C. | | |
| Split ratio | 7:1 | | |
| Gas Type | Helium | | |
| Column Parameters | | | |
| Column | ZB-624, 60 m × 0.53 mm, 3.0 μm | | |
| Mode | Constant Flow | | |
| Initial flow | 4.0 mL/min | | |
| Detector Parameters | Values | | |
| Temperature | 300° C. | | |
| Hydrogen flow | 45 mL/minute | | |
| Air flow | 450 mL/minute | | |
| Mode | Constant makeup flow | | |
| Make up flow (Nitrogen) | 10 mL/minute | | |
| Headspace Parameters | | | |
| Oven Temperature | 130° C. | | |
| Loop Temperature | 140° C. | | |
| Transfer Line Temperature | 155° C. | | |
| GC Cycle | 32 minutes | | |
| Vial Equilibration Time | 15 minutes | | |
| Vial Pressurisation Time | 0.2 minute | | |
| Loop Fill Time | 0.2 minute | | |
| Loop Equilibration Time | 0.2 minute | | |
| Injection Time | 1 minute | | |
| Agitation | High | | |

TABLE 23

Test Solutions - Prepare test solutions as described in the table below. Transfer 5 mL of test solutions to individual 20 mL GC headspace vials, preparing one vial for each injection required. Prepare sample solutions directly into GC headspace vials.

| Test Material | Replicates | Add | Make to Volume with diluent (mL) | Storage | Expiry |
| --- | --- | --- | --- | --- | --- |
| Stock Standard 1 | 1 | ~50 mL diluent 1000 mg ARS5483 | 100 | Ambient | 24-40 hours |
| Stock Standard 2 | 1 | ~50 mL diluent 360 mg of ARS5496 | 100 | Ambient | 24-40 hours |
| Working Standard | 1 | 10.0 mL of Stock Standard 1 and 1.0 mL Stock Standard 2 | 100 | Ambient | 24-40 hours |

TABLE 23-continued

Test Solutions - Prepare test solutions as described in the table below. Transfer 5 mL of test solutions to individual 20 mL GC headspace vials, preparing one vial for each injection required. Prepare sample solutions directly into GC headspace vials.

| Test Material | Replicates | Add | Make to Volume with diluent (mL) | Storage | Expiry |
|---|---|---|---|---|---|
| Samples | 2 | 250 mg (±10 mg) Alternative A 100 mg (±10 mg) Alternative B | 5 - Alternative A 2 - Alternative B | Ambient | 24-40 hours |

TABLE 24

Analysis - A typical run sequence is shown below.

| Sequence | Number of Injections |
|---|---|
| Blank | 1 |
| Standard | 1 |
| Standard | 1 |
| Working Standard | 1-6 |
| Blank | 1 |
| Sample 1 replicate 1 | 1 |
| Sample 1 replicate 2 | 1 |
| Blank | 1 |
| Sample 2 replicate 1 | 1 |
| Sample 2 replicate 2 | 1 |
| . . . up to a maximum of 7 injections between bracketing standards . . . | |
| Standard | 1 |

TABLE 25a

Data Processing (Alternative A)

| | | |
|---|---|---|
| Integration | Integrate each named solvent peak in the standard and if present in the test solutions. | |
| Typical retention times | Residual Solvent | Typical Retention Time (minutes) |
| | Tetrahydrofuran | 3.4 |
| | Isopropyl acetate | 4.0 |

| System Suitability Criteria | Ensure the following System Suitability Criteria are met: | | |
|---|---|---|---|
| | Parameter | Injections | Acceptance criteria |
| | Retention Time | First 3 Standards | RSD ≤2% for each solvent |
| | Response | First 3 Standards | RSD ≤15% for each solvent |
| | Retention Time | All standards | RSD ≤2% for each solvent |
| | Response | All standards | RSD ≤15% for each solvent |
| | Retention Time | All samples | Within ± 0.5 minutes of mean Std retention time |

TABLE 25b

Data Processing (Alternative B)

| | | |
|---|---|---|
| Integration | Integrate each named solvent peak in the standard and if present in the test solutions. | |
| Typical retention times | Residual Solvent | Typical Retention Time (minutes) |
| | Diethyl ether | 6.3 |
| | Dichloromethane | 7.4 |
| | Triethylamine | 10.3 |
| | Hexane | 8.1 |
| | Acetone | 6.7 |
| | Methanol | 5.1 |
| | Toluene | 12.6 |
| | Tetrahydrofuran | 9.5 |
| | Acetonitrile | 7.2 |
| | Ethanol | 6.1 |
| | 1-Octanol | 18.5 |

| System Suitability Criteria | Ensure the following System Suitability Criteria are met: | | |
|---|---|---|---|
| | Parameter | Injections | Acceptance criteria |
| | Retention Time | First 6 Standards | RSD ≤2% for each solvent |
| | Response | First 6 Standards | RSD ≤15% for each solvent |

TABLE 25b-continued

| Data Processing (Alternative B) | | |
|---|---|---|
| Retention Time | All standards | RSD ≤2% for each solvent |
| Response | All standards | RSD ≤15% for each solvent |
| Retention Time | All samples | Within ± 0.5 minutes of mean Std retention time |

TABLE 26

| Calculations | |
|---|---|
| Residual Solvent Content | Calculate the concentrations of Tetrahydrofuran and Isopropylacetate using the following equation: $$\text{Residual Solvent Content (ppm)} = \frac{R_{Sample} \times W_{standard} \times DF_{sample} \times 1000000}{R_{standard} \times W_{sample} \times DF_{standard}}$$ Where:<br>$R_{sample}$ = Response for solvent in sample<br>$R_{standard}$ = Mean response for all standard injections<br>W = Weight of sample or standard (mg)<br>DF = Dilution factor of sample or standard<br>Ensure the replicate results agree within 100 ppm absolute for results < 500 ppm and within ± 25% for results ≥ 500 ppm. |
| Reporting Limit (LOQ) | $$\text{Reporting Limit (ppm)} = \frac{W_{standard} \times DF_{sample} \times 1000000 \times 10}{W_{sample} \times DF_{standard} \times N}$$ Where:<br>$W_{sample}$ = Nominal sample weight (mg)<br>$W_{standard}$ = Weight of solvent in standard (mg)<br>N = Signal to noise ratio of solvent in first standard<br>DF = Dilution factor of sample or standard |

TABLE 27

| Reporting | |
|---|---|
| Residual Solvent Content | Report the amount of each residual solvent present at ≥ the reporting limit (LOQ), to the nearest integer.<br>Report all solvents not present or present at less than the reporting limit as '<LOQ'. |

Example 13: Analysis of Residual Solvents in Composition of Polymer Comprising Monomer (Ib), Prepared According to Methods of Examples 1-6, as Determined by GC Headspace Analysis

TABLE 28

| Residual Solvents | | | | |
|---|---|---|---|---|
| Residual Solvents by GC | Specification (ppm) | Results GMP lot (ppm) | Results non-GMP lot A (ppm) | Results non-GMP lot B (ppm) |
| Diethyl ether | ≤5000 | <1 | 7 | <1 |
| Dichloromethane | ≤600 | <11 | ND | <11 |
| Triethylamine | Report result | <2 | ND | <2 |
| Hexane | ≤290 | <1 | ND | <1 |
| Acetone | ≤5000 | 21 | 21 | <3 |
| Methanol | ≤3000 | 47 | 58 | <5 |
| Toluene | ≤890 | <3 | ND | <3 |
| Tetrahydrofuran | ≤720 | <2 | ND | <2 |
| Acetonitrile | ≤410 | <5 | 56 | <5 |
| Ethanol | ≤5000 | 479 | 4530 | 156 |
| 1-Octanol | Report result | <101 | ND | <101 |

ND = not detected

Non-GMP lot A, having 4530 ppm ethanol, was subjected to re-drying under vacuum under a stream of nitrogen, and converted to non-GMP lot B, having 156 ppm ethanol.

Example 14: HPLC Analytical Method for the Determination of Purity, Impurities and Leachable Degradation Products from Polymer Comprising Monomer (Ib)

TABLE 29

| Instruments, Equipment, Materials and Reagents | | |
|---|---|---|
| Instruments | HPLC | Reversed Phase HPLC system with UV detection |
| Equipment | Column | Waters XBridge C18, 100 × 4.6 mm, 3.5 μm |
| Materials | | m-Iodobenzylguanidine (mIBG) |
| | | m-Iodobenzylamine hydrochloride (mIBA) |
| | | m-Iodobenzylbiguanidine (mIBBG) |
| | | Benzylguanidine (BG) |
| | | m-hydroxybenzylguanidine (mHBG) |

TABLE 30

Preparation of Reagents

| Reagent | Description | Storage | Expiry |
|---|---|---|---|
| Mobile Phase A | 0.1% TFA/2.0% ACN in water (Typically add 1 mL TFA and 20 mL acetonitrile to 500 mL of water in a volumetric flask and dilute to 1000 mL with water) | Ambient | 7 days |
| Mobile Phase B | 0.1% TFA in Acetonitrile (Typically add 1 mL TFA to 500 mL acetonitrile in a volumetric flask and dilute to 1000 mL with acetonitrile) | Ambient | 1 month |
| Buffer C | Phosphate Buffer, pH 7.4 (Typically dissolve 0.13 g (±2%) $NaH_2PO_4$ and 0.54 g (±0.011 g) $Na_2HPO_4$ in 490 mL water, adjust pH to 7.4 if necessary with 1M NaOH or phosphoric acid and dilute to 500 mL with water) | 2-8° C. | 7 days |
| Diluent D | 1.0 mg/mL Sodium Thiosulphate in phosphate buffer (Typically dissolve 100 mg (±10 mg) sodium thiosulphate in Buffer C and dilute to 100 mL with Buffer C) | 2-8° C. | 7 days |
| Diluent E | UHQ water | Ambient | 7 days |
| Solution F | Oxidant solution Mix 1.34 mL 30% Hydrogen peroxide and 0.2 mL acetic acid in a 5 mL volumetric flask. Dilute to volume with UHQ water. | Ambient | Prepare fresh use on each day of |
| Solution G | 0.02M sodium sulphate/0.1M sodium Hydroxide in water Weigh 56.8 mg (±2.84 mg) into a 20 mL volumetric flask and dilute to volume with 0.1M sodium hydroxide. | | |
| Solution H | Sodium Iodide Stock Solution Weigh 400 mg (±40 mg) into a 20 mL volumetric flask and dilute to volume with Solution G. | | |

TABLE 31

Instrument Parameters

| Parameter | Value | | |
|---|---|---|---|
| Sample Temperature | Ambient | | |
| Column Temperature | 30° C. (±2° C.) | | |
| Flow Rate | 2.0 L/minute | | |
| Gradient | Time (minutes) | % A | % B |
| | 0 | 100 | 0 |
| | 1 | 100 | 0 |
| | 12 | 74 | 26 |
| | 13 | 50 | 50 |
| | 15 | 50 | 50 |
| | 16 | 100 | 0 |
| | 20 | 100 | 0 |
| Total Run Time | 20 minutes | | |
| Wavelength | 210 nm | | |
| Injection Volume | 20 μL and 100 μL (refer to injection sequence) | | |
| Needle Wash | 90/10 v/v Water/Acetonitrile | | |

TABLE 32

Standard Dilutions

| Test Solution | Stock Solution | Volume (mL) | Make to volume (mL) | With Diluent | Storage | Expiry |
|---|---|---|---|---|---|---|
| System Suitability Stock Solution | Primary Stock solutions | 0.2 (200 μL) of each | 10 | D | Ambient | 24 hours |
| System Suitability Solution 2% | System Suitability Stock Solution | 1.0 | 10 | D | Ambient | 4 days |
| Sensitivity solution 0.3% | System Suitability Solution 2% | 0.15 | 1 | D | Ambient | 24 hours |

TABLE 33

Purity, Impurities and Leachables Sample Solutions-
Note: Impurities are determined by iodinating the 3-benzyl guanidine supported on the resin and determining the purity and impurities of the mIBG product. Prepare the sample solutions as described in the table below.

| Solution | Replicates | Preparation | Storage | Expiry |
|---|---|---|---|---|
| Purity & Impurities Sample | 3 | As detailed below | Ambient | 75 hours |
| Purity & Impurities Matrix Blank | 2 | | Ambient | 75 hours |
| Leachables Sample | 2 | | Ambient | 49 hours |
| Leachables Blank | 1 | | Ambient | 49 hours |

Purity and impurities Sample and Matrix Blank Preparation procedure

- Weigh 80 mg (±8.0 mg) sample into a 20 mL volumetric flask. For blank matrix preparation, omit sample.
- Add in the following order:
1) 0.5 mL ethanol, swirl and stand for 5 minutes minimum to wet.
2) 2.0 mL water (Diluent E).
3) 1.0 mL solution H.
4) 0.5 mL Solution F.
- Vortex the mixture for 5 seconds.
- Mix reaction mixture on a flask shaker at 500 for 60 minutes.
- Dilute to volume with UHQ water (Diluent E).
- Transfer the mixture to a centrifuge tube and centrifuge for 15 minutes at 4000 rpm.

TABLE 33-continued

Purity, Impurities and Leachables Sample Solutions-
Note: Impurities are determined by iodinating the 3-benzyl
guanidine supported on the resin and determining the purity
and impurities of the mIBG product. Prepare the sample
solutions as described in the table below.

| Solution | Replicates | Preparation | Storage | Expiry |
|---|---|---|---|---|
| • Dilute 4.0 mL supernatant liquid of blank and one of the samples only to 25 mL with Diluent D.<br>• Analyze the prepared sample according to Sample Concentration Check sequence.<br>• Calculate volume of stock sample required for each of two remaining samples to obtain a mIBG concentration of 100 µg/mL ± 20%.<br>• Prepare the blank and the other two samples by diluting calculated volume of supernatant liquid to 25 mL with Diluent D.<br>• Analyze the prepared samples according to Purity, Impurities and Leachables sequence.<br>Leachables Sample and Blank Preparation procedure | | | | |
| • Weigh 20 mg (±2.0 mg) sample into a COC vial. For blank preparation, omit<br>• Add 7.5 mL water (Diluent E).<br>• Mix for 5 seconds.<br>• Incubate the vials at room temperature at 20-28° C. for 60 ± 10 min.<br>• Filter the samples and blank through a 0.2 µm PTFE syringe filter.<br>• Analyze samples without any further dilution. | | | | |

TABLE 34

Data Processing

Typical retention time | Typical retention time of mIBG: ~10.3 minutes | | |
|---|---|---|---|
| | Peak | RT (min) | RRT |
| | mHBG | 3.85 | 0.38 |
| | BG | 5.85 | 0.57 |
| | mIBA | 8.16 | 0.79 |
| | mIBBG | 9.54 | 0.93 |

Example 15: Determination of Purity, Impurities and Leachable Degradation Products in Compositions of Polymer Comprising Monomer (Ib), Prepared According to the Methods of Examples 1-6

TABLE 35a

Purity, Impurities and Leachable Degradation Products in Polymer (Ib) at time = 0 months

| Test | Specification | Results GMP lot | Results non-GMP lot |
|---|---|---|---|
| Purity by HPLC: reaction with iodine | ≥98% MIBG (iobenguane)<br>≤1.0% MIBA<br>≤1.0% MIBBG<br>Report unknown impurities ≥0.3% area | MIBG 99.2%<br>MIBA 0.27%<br>MIBBG < 0.15%<br>Unknown impurities:<br>0.26% Area | MIBG 99.1%<br>MIBA 0.39%<br>MIBBG < 0.16%<br>Unknown impurities:<br>0.34% Area |
| Leachable TOC in water | ≤1% | <0.01% | 0.24% |
| HPLC assay of leachable degradation products | Benzyl-guanidine ≤ 0.1% (≤0.04 µg/mL)<br>Meta-hydroxy-benzyl-guanidine ≤ 0.1% | Benzyl-guanidine: Not Detected<br>Meta-hydroxy-benzylguanidine: Not Detected | Benzyl-guanidine: <0.01%<br>Meta-hydroxy-benzylguanidine: <0.01% |
| | (≤0.04 µg/mL) Total unknown impurities ≤0.5% (≤0.2 µg/mL) | Total unknown impurities: 0.01% | Total unknown impurities: ND |

ND = not detected

TABLE 35b

Purity and Impurities in Polymer (Ib) over time

| | Storage Conditions and Results (GMP lot, purity over time at various conditions) | | |
|---|---|---|---|
| Duration (in months) & | −20° C. | 25° C. 60% Relative Humidity | 40° C. 75% Relative Humidity |
| 0 | | | |
| MIBG % | 99.2 | 99.2 | 99.2 |
| MIBA % | 0.27 | 0.27 | 0.27 |
| MIBBG % | <0.15 | <0.15 | <0.15 |
| Unknown impurities: % Area | 0.26 | 0.26 | 0.26 |
| 1 | | | |
| MIBG % | 99.2 | 99.5 | 99.4 |
| MIBA % | <0.3 | <0.3 | <0.3 |
| MIBBG % | <0.3 | <0.3 | <0.15 |
| Unknown impurities: % Area | 0.27 | <0.3 | <0.28 |
| 3 | | | |
| MIBG % | 99.2 | 99.3 | 99.1 |
| MIBA % | <0.3 | 0.25 | <0.3 |
| MIBBG % | <0.3 | <0.3 | <0.3 |
| Unknown impurities: % Area | <0.3; <0.3 (two runs) | <0.3; <0.3 (two runs) | 0.32; <0.3; <0.3 (three runs) |
| 6 | | | |
| MIBG % | 99.3 | 99.3 | 98.8 |
| MIBA % | <0.3 | <0.3 | <0.3 |
| MIBBG % | <0.3 | <0.3 | <0.3 |
| Unknown impurities: % Area | <0.3; <0.3 (two runs) | <0.3; 0.26 (two runs) | 0.59; <0.3; <0.3 (three runs) |
| 9 | | | |
| MIBG % | 99.0 | 98.8 | |
| MIBA % | 0.3 | 0.3 | |
| MIBBG % | <0.3 | <0.3 | |
| Unknown impurities: % Area | <0.3; 0.3; <0.3 (three runs) | five runs, all <0.3 | |

Example 16: Iobenguane Formulation

Iobenguane was prepared from (Ultratrace®) polymer comprising monomer (Ib), where the polymer was prepared according to the methods of Examples 1-6. Iobenguane was formulated and sealed in vials as described below in Table 36.

TABLE 36

| Iobenguane Formulation | | | |
|---|---|---|---|
| Total Fill Volume (Dosimetry) | 1.5-2.5 mL/vial | Total Fill Volume (Therapeutic) | 20-25 mL/vial |
| Active Pharmaceutical Ingredient: | [I-131]-MIBG | Storage Condition | <−70° C. |
| Container Closure | 30 mL sterile, empty evacuated vial (Hollister Stier P/N 7521ZA) 20 mm Lyo NovaPure Stopper (West/19700311) 20 mm Aluminum seal (Wheaton/224178-01) | | |

| Specification | Acceptance Criteria | Standard Test Method | Method Type |
|---|---|---|---|
| DESCRIPTION | | | |
| Appearance | Clear solution, free of visible particles | QC-STM-0034 | Visual Inspection |
| IDENTIFICATION TESTS | | | |
| Radiochemical Identification | [I-131]-MIBG retention time is 90-110% of reference standard | QC-STM-0026 | HPLC-UV-Radiometric Detection |
| Radionuclidic Identity | Gamma Photon Emission at 364 ± 10 keV | USP <821> | Gamma spectroscopy |
| ASSAY @ TOC | | | |
| MIBG concentration | 0.001-0.010 mg/mL | QC-STM-0026 | HPLC-UV |
| Ascorbate | 48-64 mg/mL | QC-STM-0016 | HPLC-UV |
| Gentisate | 20-25 mg/mL | QC-STM-0016 | HPLC-UV |
| Radioactive Concentration | 13.5-16.5 mCi/mL @ TOC | QC-STM-0026 | Dose Calibrator |
| Total Radioactivity (Dosimetry) | 20-42 mCi/vial @ TOC | USP <821> | Dose Calibrator |
| Total Radioactivity (Therapeutic) | 270-413 mCi/vial @ TOC | USP <821> | Dose Calibrator |
| PHYSICAL TESTS | | | |
| pH | 4.5-5.5 | QC-STM-0021 | pH meter |
| RADIOCHEMICAL PURITY TESTS | | | |
| Radiochemical Purity | ≥96% | QC-STM-0026 | HPLC-Radiometric Detection |
| Total radiochemical impurities (free I-131 and other impurities) | ≤4% | QC-STM-0026 | HPLC-Radiometric Detection |
| MICROBIOLOGICAL TESTS | | | |
| Bacterial Endotoxins | ≤2 EU/mL | STM-MIC-GEN-10-0001 | USP <85> by gel-clot method |
| Sterility | No growth | MIC-STM-0005 | USP <71> by Membrane Filtration |
| Filter Integrity Test | ≥47 psi | PRD-STM-0001 | Bubble Point |

Example 17: Phase II Study Evaluating the Efficacy and Safety of Ultratrace® Iobenguane I-131 in Patients with Malignant Relapsed or Refractory Pheochromocytoma/Paraganglioma Objectives—Primary Objective:

To determine the proportion of study subjects with a reduction (including discontinuation) of all antihypertensive medication by at least 50% for at least six months or two cycles, from two Therapeutic Doses each at 500 mCi (or 8 mCi/kg, for subjects weighing 62.5 kg or less) of Ultratrace iobenguane I 131 administered approximately three months apart.

Objectives—Secondary Objectives:

To evaluate the safety of Ultratrace iobenguane I 131 in subjects with malignant pheochromocytoma/paraganglioma, including human radiation absorbed dose-estimates to normal organs.

To assess the proportion of subject with overall tumor response of complete response (CR) or partial response (PR) per RECIST criteria.

To assess the proportion of subjects with overall tumor response of CR, PR or MR, (moderate response, i.e., decrease in the sum of the longest diameters of the target lesions of 15-30%, with no evidence of progressive disease [PD] in non-target per RECIST criteria.

To assess bone lesion status on the Soloway Scale.

To assess tumor marker response in 24 br urine and other serum/plasma tumor markers associated with pheochromocytoma/paraganglioma.

To describe changes from baseline in the overall quality of life through the EORTC QLQ-C30 questionnaire post-treatment.

To describe changes from baseline in symptoms using the National Institute of Health (NIH) Quality of Life and Symptoms Questionnaire of Pheochromocytoma and Paraganglioma post treatment.

To assess change in use of analgesics and pain medications.

To describe Karnofsky Performance Status post-treatment.

To assess overall survival, up to 5 years post-treatment.

Study Design

This is a multi-center, open-label, single arm study. It is anticipated that approximately 75 subjects will be enrolled to ensure fifty-eight subjects given two Therapeutic Doses each at 500 mCi (or 8 mCi/kg for subjects weighing 62.5 kg or less) of Ultratrace iobenguane I 131 will be evaluable for efficacy and safety. Prior to administration of the first Therapeutic Dose, subjects will be given an Imaging Dose (3 mCi-6 mCi) of: Ultratrace iobenguane I 131 and will undergo iobenguane I 131 scintigraphic scans to evaluate tumor avidity as wells to measure normal organ distribution and allow for the calculation of radiation dosimetry to normal organs. Both Therapeutic Doses for a subject will be appropriately decreased by the same amount if results of the dosimetry study indicate an adjustment is warranted.

Tumors will be measured by computed tomography (CT) or magnetic resonance (MR) at baseline and at 3, 6, 9 and 12 months after the first Therapeutic Dose. A bone scan will be performed at Screening/baseline, and if probable metastatic disease is observed additional bone scans will be performed at Months 3, 6, 9, and 12. Overall tumor response at 3, 6, 9 and 12 months per RECIST criteria will be assessed centrally by independent, blinded readers. If the study site has the capability to perform flurodeoxyglucose (FDG) scans, they may be performed to assess viable tumor tissue at baseline and 3, 6, 9, and 12 months. Tumor markers [serum chromogranin A, plasma free metanephrines and normetanephrines, 24 hour urinary vanillylmandelic acid (VMA), plasma catecholamines (dopamine, epinephrine and norepinephrine), 24 hour urinary catecholamines (dopamine, epinephrine and norepinephrine) and urinary metanephrines and normetanephrines will be evaluated by a central laboratory at intervals described in the protocol. Renal function will be assessed through either creatinine clearance or Glomerular Filtration Rate (GFR) at baseline and at the Months 6 and 12 Effficacy Visits. Evaluation of thyroid function (T3 T4 and TSH) and clinical evaluation of possible dry mouth will be performed at the 12 month Efficacy Visit. Use and dose of antihypertensive, pain and other medication required for tumor associated signs and symptoms will be recorded on an on-going basis, including on an outpatient basis. Subject-reported Quality of Life measurements will be obtained through the EORTC QLQ-C30 v3 and the NIH Quality of Life and Symptoms Questionnaire for Pheochromocytoma and Paraganglioma. The frequency of the procedures is summarized in the Schedule of Procedures.

Safety will be assessed through analyses of treatment emergent adverse events (AEs), as well as baseline and pre- and post-infusion ECGs, physical examinations, vital signs measurements, laboratory measurements (including clinical chemistry, hematology and urinalysis), and human radiation absorbed dose estimates to target lesions and normal organs.

Study Duration

Subjects will attend study visits from the time of signed informed consent through 12 months after the first Therapeutic Dose of Ultratrace iobenguane I 131. They will then enter long-term follow-up, and remain in follow-up for 5 years after the first therapeutic dose.

Inclusion Criteria

All subjects must:
1. Provide written informed consent (and assent for subjects less than 18 years of age) and be willing to comply with protocol requirements.
2. Be at least 12 years of age.
3. Have a documented (medical record) diagnosis of either pheochromocytoma or paraganglioma that was confirmed by histology or a physician using other supportive data (e.g., abnormal metaiodobenzyl guanidine (MIBG) diagnostic study, or elevated tumor markers).
4. Be ineligible for curative surgery for pheochromocytoma.
5. Have failed a prior therapy for pheochromocytoma/paraganglioma or are not candidates for chemotherapy or other curative therapies.
6. Be on stable antihypertensive medication regimen for tumor-related hypertension for at least 30 days prior to the first therapeutic dose. A stable antihypertensive medication regimen is defined as no addition or deletion of antihypertensive medication and no change in total daily dose or route of administration for currently used antihypertensive medication(s) in the 30 days prior to first therapeutic dose.
7. Have at least one tumor site by CT or MR or iobenguane I 131 scan.
8. Have definitive MIBG tumor avidity.
9. Have an expected survival period of at least 6 months as prognosticated by physician.

Exclusion Criteria

Subjects will be excluded if any of the following conditions are observed:
1. <50% of FDG (if data are available) positive lesions are MIBG avid.
2. Pregnant or nursing females.
3. Active central nervous system (CNS) lesions by CT or MR scanning within 3 months of study entry.
4. New York Heart Association class IV heart failure, symptomatic congestive heart failure [New York Heart Association class IV with another medical disorder], unstable angina pectoris, cardiac arrhythmia.
5. Received any previous systemic radiotherapy resulting in marrow toxicity within 3 months of study-entry or have active malignancy (other than pheochromocytoma/paraganglioma) requiring additional treatment during the active phase or follow up period of the Ultratrace iobenguane I 131 trial. (Prior iobenguane I 131 therapy is allowed if not within 3 months prior to the first therapeutic dose).
6. Administered prior whole-body radiation therapy.
7. Received external beam radiotherapy to >25% of bone marrow.
8. Administered prior chemotherapy within 30 days of study entry or have active malignancy (other than pheochromocytoma/paraganglioma) requiring additional treatment.
9. Karnofsky Performance Status is <60.
10. Platelets <80,000/µL.
11. Absolute neutrophil count (ANC)<1,200/µL.
12. Total bilirubin>1.5 times the upper limit of normal.
13. AST/SGOT or ALT/SGPT>2.5 times the upper limit of normal.
14. Diagnosed with AIDS or HIV-positive per patient medical history.
15. Active chronic alcohol abuse, chronic liver disease (excluding liver metastases), or hepatitis (A, B or C, detected by positive testing for HbsAg and anti-HCV as stated in patient medical history).
16. Renal dysfunction/impairment (defined as creatinine clearance of <30 mL/min or Glomerular Filtration Rate (GFR) of <30 mL/min) because of the possibility of delayed Ultratrace iobenguane I 131 excretion and increased whole body dose.
17. Known allergy to iobenguane that has required medical intervention.
18. Received a therapeutic investigational compound and/or medical device within 30 days before admission into this study.
19. Receiving a medication which inhibits tumor uptake of iobenguane I 131.
20. Any medical condition or other circumstances (i.e., uncontrolled current illness including but not limited to, ongoing or active infection or psychiatric illness/social situations that would limit compliance with the study requirements).
21. Any other condition, that in the opinion of the investigator, may compromise the safety or compliance of the subject or would preclude the subject from successful completion of the study.

Study Drug

Each subject will be administered 3 mCi to 6 mCi Ultratrace iobenguane I 131, referred to as the Imaging Dose, to confirm that subject meets radiological entry criteria and to establish dosimetry. All subjects meeting entry criteria will then receive the investigational product referred to as the Therapeutic Dose (500 mCi or 8 mCi/kg if the subject weighs 62.5 kg or less) of Ultratrace iobenguane I 131, followed by imaging within 7 days post infusion. The Therapeutic Doses will be adjusted equally if warranted by results of the dosimetry evaluation. At least 3 months later, subjects will receive the second Therapeutic Dose.

Imaging Parameters

During the baseline period, CT or MR scans of the chest, abdomen and pelvis with IV contrast (unless medical condition or allergy prevents its use) and a bone scan will be acquired to determine extent of disease. Obtaining renal volume for each kidney is required. Anatomical volumes may be measured for other organs and tissues to further evaluate absorbed dose.

After the Imaging Dose (3 mCi to 6 mCi) of Ultratrace iobenguane I 131, subjects will have an Ultratrace iobenguane I 131 anterior and posterior planar whole body scan at 1 hour, 1-2 days and 2-5 days following the dose to evaluate biodistribution and (for the first dose) to confirm uptake in at least one known tumor that meets RECIST criteria. At least 18 hours separation between each of the image acquisitions is required. The tumor to background ratio should be ≥2, and may be best visualized beginning at the 24 hour image to allow background clearance. For example, a liver lesion should be 2× background normal liver while soft tissue lesions would use background in surrounding soft tissue.

Subjects will have an Ultratrace iobenguane I 131 whole body scan within 7 days following each Therapeutic Dose to further assess biodistribution.

Subjects will have follow-up CT or MR scans at 3, 6, 9 and 12 months after the first Therapeutic Dose of Ultratrace iobenguane I 131 to assess tumor response. Subjects may also have optional follow up FDG scans at 3, 6, 9 and 12 months after the first Therapeutic Dose of Ultratrace iobenguane I 131. Bone scans will be performed at Month 3, 6, 9, 12, if probable metastatic disease is observed on the Screening bone scan. Subjects may undergo additional scars at unscheduled visits for confirmation of response.

All images will be sent to the central imaging core lab for evaluation after anonymization. Off-site. CT or MR assessment will be conducted by independent, CT and MR-experienced readers in accordance with the charter issued by the imaging core laboratory. These readers will be blinded to clinical subject information as described in the Imaging Charter. The readers will determine objective tumor response according to RECIST criteria. On-site interpretation of CT or MR images may also be performed, but only the results of the blinded read will be used for the objective tumor response evaluations.

As part of long-term follow-up, a subject may receive additional scans to monitor disease status per institutional standard of care; these images will not be evaluated by a central laboratory.

Endpoints—Primary Endpoint:

The primary endpoint for this trial is the proportion of study subjects with a reduction (including discontinuation) of all antihypertensive medication by at least 50% for at least six months or two cycles Ultratrace iobenguane I 131. The primary endpoint will be assessed at the time of study completion or discontinuation, whichever occurs first.

Endpoints—Secondary Endpoints:

Proportion of subjects with overall tumor response of CR or PR per RECIST criteria Proportion of subjects with overall tumor response of CR, PR or MR (moderate response) per RECIST criteria Bone lesion response per the Soloway Scale Tumor marker response in 24 hr urine and other serum/plasma tumor markers associated with pheochromocytoma/paraganglioma Status of hypertension and changes in blood pressure Quality of-Life per the recommended guidelines from the EORTC QLQ-C30 manual Symptoms as evaluated through the NIH Quality of Life and Symptoms Questionnaire for Pheochromocytoma and Paraganglioma.

Change in use of analgesics and pain medications

Overall survival (OS), defined as the time from the date of enrollment to the date of death from any cause. OS time will be censored at the last date the subject is known to be alive when the confirmation is absent or unknown.

Safety assessed by changes in lab values, physical exams or vital signs, and the occurrence of treatment emergent adverse events.

Human radiation absorbed dose estimates to normal organs

Sample Size

It is anticipated that approximately 75 subjects will be enrolled to ensure that 58 subjects receive two doses and are evaluable for safety and efficacy. The one-sided alternative hypothesis of the study is that the proportion of subjects experiencing a reduction (including discontinuation) of all antihypertensive medication by at least 50% for at least six months or two cycles is 0.25, against the null hypothesis that the proportion is 0.10. Sample size of 58 subjects in the Per Protocol Set was based on a one-sided significance level of α=0.025 and power of 0.90 (90%).

Example 18: Comparison of Leachable Tin Levels in Compositions Comprising MIBG

Provided are exemplary methods to compare leachable tin levels in compositions comprising MIBG prepared from polymer comprising a monomer of formula (I). Such polymers may be prepared, for example, according to (a) methods described in U.S. Pat. No. 7,658,910, (to yield relatively high levels of leachable tin) or (b) methods of Examples 1-6 (to yield relatively low levels of leachable tin).

Low levels of leachable tin are desirable in the cleaved MIBG product formed by iodination of a relatively tin-free dialkylstannane-functionalized polymeric drug substance precursor (DSP), prepared according to methods of Examples 1-6. Low levels of leachable tin in the DSP are expected to afford an iodinated drug substance likewise containing low levels of tin. Tin is a Class 3 impurity according to U.S. and other regulatory authorities.

By contrast, relatively high levels of leachable tin in the polymer methods prepared according to methods described in U.S. Pat. No. 7,658,910 may carry through to the MIBG drug substance after its cleavage from the resin by iodination. Tin levels in MIBG may be investigated in order to provide quantitative data on the extent to which high and low levels of leachable tin content in the polymer precursor affect the leachable tin levels in the MIBG drug substance.

Without being bound by theory, leachable tin levels in polymer comprising a monomer of formula (I) generally derive from solvolysis of the organostannane linkage between the arylguanidine moiety and the poly(divinylbenzene) resin. This solvolysis reaction can be mediated by residual solvents, e.g., ethanol and water, both of which may be used, in some embodiments, in the final washing sequence prior to vacuum drying. A comparison of washing and drying steps are provided in Table 1 below for methods described in U.S. Pat. No. 7,658,910 relative to those in Examples 1-6.

|  | Washing | Drying |
|---|---|---|
| Methods described in U.S. Patent No. 7,658,910 | 95:5 EtOH:H$_2$O (10 washes by Buchner filtration) | Vacuum desiccator at ambient temperature, to constant weight |
| Methods of Examples 1-6 | 95:5 EtOH:H$_2$O (8 washes by centrifugation) EtOH (anhydrous) (6 washes by Buchner filtration) | 3 Stage Drying sequence in Vacuum Oven 1) Ambient temperature with N$_2$ flow, no vacuum, 1-2 hours 2) Ambient temperature with N$_2$ flow, full vacuum, ≥ 14 hours 3) 30 ± 3° C. with N$_2$ flow, full vacuum, ≥ 14 hours to constant weight |

A single batch of polymer comprising a monomer of formula (I) can be manufactured through an ion exchange step whereby polymer-supported benzylguanidinium chloride is exchanged to the acetate salt form. Prior to the final washing and drying sequence, the resin can be split into two sub-lots and the final washing and drying sequence performed separately on each sub-lot according to (a) methods described in U.S. Pat. No. 7,658,910 or (b) methods of Examples 1-6. Both sub-lots can be analyzed by full release testing. In this manner, batches of resin can be manufactured according to (a) methods described in U.S. Pat. No. 7,658,910 (yielding relatively high levels of residual tin) or (b) methods of Examples 1-6 (yielding relatively low levels of residual tin).

Both of sub-lots (a) and (b) can then be subjected to iodination using the method of Example 14 above; the respective MIBG solutions thus formed can then each be tested by ICP-MS for tin content using methods, such as that of Example 19 below. As leachable tin has been observed by Applicants to increase substantially during storage when the resin is packaged after the washing and drying procedures in U.S. Pat. No. 7,658,910, a further aspect of this experiment would be to perform a stability study, whereby respective resins are stored for 1, 3, and 6 months at reduced temperatures (e.g., −20° C.). At each timepoint the analyses can be performed, including (1) analyses of each resin for leachable tin content, and following iodination of each polymer, (2) tin content testing on each of the cleaved MIBG drug substances or pharmaceutical compositions comprising the same.

Example 19: Representative ICP-MS Protocols

1. Scope

This procedure is suitable for the determination of elements detectable by ICP-MS in matrices that yield relatively clear aqueous solutions by dissolution, acid digestion and microwave digestion. The method also covers matrices that yield clear solutions in organic solvents with low carbon content such as Methanol, Ethanol and DMSO.

ICP-MS can be used to conduct analyses for, but is not limited to, the following elements Al, Au, As, B, Ba, Be, Bi, Ca, Cd, Ce, Co, Cr, Cs, Cu, Er, Eu, Fe, Ga, Gd, Hg, Ho, Hf, In, Ir, K, La, Li, Lu, Mg, Mn, Mo, Na, Nd, Ni, Os, P, Pb, Pd, Pr, Pt, Re, Rb, Rh, Ru, Sb, Se, Sm, Sn, Sr, Ta, Te, Th, TL, Tm, U, V, W, Zn and Zr.

The range of this technique is generally effective for, but not limited to, a concentration of analyte between 0.1 mg/kg-1000 mg/kg in sample.

The analyst should be aware that certain element combinations may result in poor solubility after digestion e.g., silver and chloride, barium and sulphur. However, 10% HCl will keep up to 10 μg/mL Ag in aqueous solution due to complexation (Ag+ in solution as the $Ag(Cl)^{X-(X-1)}$).

Elements not suited to this method include: Silicon, which can precipitate in acid solutions, and Titanium (if from $TiO_2$) which has poor solubility.

Not all organic materials can be digested using microwave techniques. For aqueous solutions, the following are special cases and may need to be prepared separately: Osmium: Nitric acid should not be used. Use Hydrochloric acid instead. Silver: dilute Hydrochloric acid should be avoided. Tin: solution should be prepared in 10-20% Hydrochloric Acid.

2. Instruments, Equipment, Materials and Reagents

| | | Description |
|---|---|---|
| Instruments | ICP-MS | Agilent 7900 |
| | Balance | Minimum 5 place balance |
| | Microwave | Mars 5 |
| Equipment | Plastic ware | Various sizes of volumetric flasks and measuring cylinders |
| | Plastic Centrifuge Tubes | 50 mL, 15 mL and 10 mL tubes of suitable grade with volume markings. |
| | Auto Pipettes | Varying capacity from 50 μL to 10000 μL |
| Materials | | 10 ppm, 1000 ppm or 10000 ppm stock standards (single or multi-element solutions). Other stocks can be used if CoA is provided. |
| Reagents | Water | UHQ |
| | Nitric Acid 67-70% | ICP-MS Grade |
| | Hydrochloric Acid 35% | ICP-MS Grade |
| | Hydrogen Peroxide 30% Other ICP grade reagents can be used if required. | ICP-MS Grade |

3. Instrument Setup for Organic (e.g. Methanol, Ethanol and DMSO or their Mixtures with Aqueous Acidic Solutions)

Change torch to 1.5 mm ID, remove ISTD tubing, put the needle into a 1 ppb Agilent tune solution (aqueous), turn on the plasma and do only Torch Axis Setting of the start-up. Switch off the plasma and wait for standby. Change the plasma mode in the hardware window to organic solvent and switch off SC cooling (for DMSO only).

Load and Adjust Suitable Organic Solvent Template

Prepare 1 ppb tune solution by diluting with the organic matrix (DMSO, Ethanol or other solvents). Add 1% $HNO_3$ to the organic tune solution for better stability. Go to Tune, run Auto Tune then save the template as a batch with suitable name. Edit sample list and add to the queue. Note:

It is recommended to add 1-5% acid to all organic samples and standards for better stability Waste tubing should be organic for DMSO.

Sample tubing should be Tygon MH3 (Glass Expansion) or equivalent.

Ni cones can be used for Ethanol and DMSO. However, Pt cones are better and they should be used for solvents with higher carbon content.

4. Preparation of Reagents

| Reagent | Description | Storage | Expiry |
|---|---|---|---|
| Diluent A | Water (or organic if instrument is set up for organics) | Ambient | 7 days |

The diluent for samples and calibration standards/internal standards/QCs should be matched if possible.

5. Standards Preparation 5.1 General Consideration

Analysts should be careful when using mixed element standards that the final matrix is suitable for all the elements in that standard regardless of whether they are needed in the analysis e.g. silver will precipitate from dilute hydrochloric acid solutions.

Standard solutions should be matrix matched as closely as possible to the samples with respect to nitric and hydrochloric acid concentration (or organic content in case organic solvents are used).

As a minimum, the following calibration solutions are required:
Calibration blank
Two calibration standards
Independent check standard as per above sections
Reporting/specification limit standard as per above sections. This standard may be used as one of the calibration standards (can be skipped if the limit is too high to be included in the analysis).

All standard solutions require the addition of one or more internal standards. Alternatively, online internal standard addition can be used.

Typically, standards prepared at 1.0 ppb and 10 ppb provide an acceptable range. If only trace levels are expected, the 10 ppb standard may be replaced with a 0.1 ppb standard. If higher levels are expected, the 1 ppb may be replaced with a 100 ppb standard. These concentrations are only meant as a guide. Alternative concentrations may be prepared if more applicable to the range and reporting requirement of the customer.

To reduce the risk of contamination, calibration solutions are made up in capped 50 mL plastic centrifuge tubes. The tubes have calibrated volumetric markings and must be used for dilution of solutions that do not contain internal standard or where internal standard is introduced online. The volume scale on uncalibrated tubes may be used for the final dilution as accurate dilution to the final volume is not necessary where internal standard is added.

Acid concentrations should not exceed 10% v/v for ICP-MS analysis while implementing nickel cones.

All standard preparations must be clearly documented in the analyst's raw data. Standards at higher concentrations may be prepared where results are over range, but linearity must be demonstrated. This can be achieved by adding the additional standard solutions to the analytical run. If the response is within 10% of expected, linearity is confirmed.

5.2 Preparation of Internal Standard

The following may be used as a dilution scheme for preparing internal standards; however alternative schemes that do not compromise on accuracy are also acceptable:

Prepare the internal standard and standard solutions as described in the table below. These internal standard solutions provide a range of masses suitable for routine use, however, alternative elements may be used if deemed more appropriate.

| Solution | Replicates | Add | Make to Volume (mL) | With Diluent | Storage | Expiry |
|---|---|---|---|---|---|---|
| 1000 ppb Mixed Internal Standard | 1 | 5 mL of 10 ppm stock (Scandium, yttrium, indium, terbium and bismuth standards) + 1 mL of nitric acid | 50 | A | Ambient | 7 days |
| 200 ppb Mixed Internal Standard for Online Addition | 1 | 1 mL of 10 ppm stock (Scandium, yttrium, indium, terbium and bismuth standards) + 1 mL of nitric acid | 50 | A | Ambient | 7 days |

5.3 Calibration Standards—Preparation

The following may be used as a dilution scheme for preparing calibration standards; however alternative schemes that do not compromise on accuracy are also acceptable: Prepare the stock standard solution (secondary mix standard) as described in the table below.

| Solution | Replicates | Add | Make to Volume (mL) | With Diluent | Storage | Expiry |
|---|---|---|---|---|---|---|
| 1000 ppb Secondary Mixed Standard (100 ppb Hg) | 1 | 0.5 mL 10 ppm Hg + 5 mL of stock metal standard (10 ppm) as required + 1 mL of nitric acid | 50 | A | Ambient | 7 days |

Calibration Blank
Add acid to deionised water in a 50 mL centrifuge tube to match the concentration in the final sample preparations. Add 0.5 mL of the mixed internal standard solution and dilute to volume with water.

1 ppb Mixed Working Standard (0.1 ppb Hg)
Add 0.05 mL of the secondary mixed standard to a 50 mL plastic centrifuge tube. Add acid as for the calibration blank and 0.5 mL of the mixed internal standard solution. Dilute to volume.

10 ppb Mixed Working Standard (1 ppb Hg)
Add 0.50 mL of the secondary mixed standard to a 50 mL plastic centrifuge tube. Add acid as for calibration blank and 0.5 mL of the mixed internal standard solution. Dilute to volume.

100 ppb Mixed Working Standard (10 ppb Hg)
Add 5.00 mL of the secondary mixed standard to a 50 mL plastic centrifuge tube. Add acid as for calibration blank and 0.5 mL of the mixed internal standard solution. Dilute to volume.

Expiry
The calibration standards should be prepared fresh for each analysis and not stored for longer than 24 hours. Note:

it is advised that Mercury calibrations do not exceed 10 ppb due to its longer washout times in the instrument. Calibration solutions containing mercury will require a matrix containing 1% hydrochloric acid.

6. Quality Control Preparation

An independent QC (IQC) standard should be prepared from an alternate stock source and analysed after the calibration. Results for IQC standards must be within 85-115% of the expected (certified) value.

One sample must be analysed in duplicate for every batch or part of a batch of 10 provided sufficient material is available. Typically, the difference between two results should be within 10% of the mean, but this will not always be achievable (when measuring near the instrument quantitation limit, for example).

| Number of Samples | Number of Duplicates |
| --- | --- |
| 1-10 | 1 |
| 11-20 | 2 |
| 21-30 | 3 |
| 31-40 | 4 |

If matrix effects are anticipated, a sample should be spiked with each element to be determined before digestion or dissolution (if appropriate). Spike recovery must be within 85-115% of target for quantitative analysis. The spike concentration should be appropriate to the requirement of the test. For limit tests a spike at the specification limit would be appropriate. Spike recoveries provide information regarding collective effect of matrix interferences and analytical procedures recoveries, and should be performed at least once for each matrix type in the batch if matrix effects are anticipated. Recoveries are normally calculated as a percentage of spike added, against spike detected after subtraction of the contribution from the sample. However, where the contribution from the sample exceeds the spike amount added, the recovery may be expressed as a percentage of the total element detected against the total element expected. When spiking at the specification for limit tests, lower recoveries may be accepted provided that the concentration of the element in the test solution is less than half the concentration in the spike solution.

If a clear solution cannot be obtained, a sample should be spiked with each element to be determined before preparation. Centrifuging slightly turbid solutions are acceptable and data will be verified from the performance of the spike recovery which must be within 85-115% of target.

Internal standard is required for all analysis and is added at a suitable concentration. Recovery of the internal standard must be in the range 70%-130%. Alternatively, online internal standard addition can be used and MassHunter will monitor internal standard variation between runs. This should be in the range 70%-130%.

A calibration standard should be prepared at the required reporting/specification limit (if applicable). The calculated concentration must be within 80-120% (can be skipped if the limit is too high to be included in the analysis).

7. Sample Preparation and Handling

If complete dissolution is achieved using diluted acid (e.g. 10% HNO3). Digestion is not required.

Acid digestion using concentrated acid can be an alternative if dissolution is not achievable using diluted acid.

Microwave digestion is to be used if acid digestion does not give clear solution. Refer to AOI-189 for microwave digestion. Check that the material is suitable for digestion.

Organic solvents are an alternative option instead of digestion where suitable.

Ensure the sample is homogenous. Lumpy samples should be crushed and blended with a plastic spatula prior to sampling.

The EasyPrep should be acid cleaned prior to use. A cleaning run using the digestion acid mix to be used for samples should be performed. Note: acids used for cleaning should not be the high purity grades used for sample analysis. Analar grades or equivalent are considered suitable for this purpose.

When performing trace analysis, the maximum sample weight that can be digested is approximately 0.5 g. Typically, this will be digested in 10 mL of acid.

Prepare a spike and duplicate preparation using the same size aliquot where possible as required by the QC requirements. The spike is prepared by adding a suitable aliquot of the secondary mixed standard prior to the addition of digestion. It is recommended that the quantity of spike added matches the specification limit for the sample, or a quantity equivalent to the amount expected in the sample.

If a reduced volume of acid is used, purified water must be added to make the total volume of liquid 10 mL.

Digest the samples in accordance with microwave digestion AOI-189 at 210° C.

When digestion is complete, the sample is transferred to a 50 mL plastic centrifuge tube. If mercury is to be determined, hydrochloric acid should be added so that the preparation has a nominal concentration of 10% hydrochloric acid. For example, if 10 mL nitric acid has been used in digestion, then 5 mL of hydrochloric acid should be added at this stage. Where reverse aquaregia has been used, an additional 2 mL of nitric acid and 3 mL of hydrochloric should be added. The solution is diluted to 50 mL with water. Samples requiring tin or silver will require a further 5 mL of hydrochloric acid to be added before making up to volume to give a 20% hydrochloric acid solution.

Further dilute the preparation so that the acid concentration does not exceed 10% v/v. In general, 1.0 mL of the digest stock and 0.10 mL of the mixed internal standard solution is diluted to 10 mL with water. Alternate dilution ratio may require adjustment to the acid volume added. See sections above. In general working solutions should contain 2% nitric acid and 1% hydrochloric acid (if mercury is required).

All solutions prepared for MS analysis must be clear without any precipitate. The presence of insoluble material in the digested sample may mean that the preparation method is unsuitable for analysis or incomplete. Further digestion after adding 2 mL hydrogen peroxide may be tried.

If a clear solution cannot be obtained, centrifuging slightly turbid solutions are acceptable (see sections above). Data will be verified from the performance of the spike recovery.

General Notes:

The sample preparation technique detailed above is intended as a generic outline; any combination of acids may be employed if it is known to be beneficial and provides a clear aqueous solution after digestion.

For most applications nitric acid alone is suitable, but nitric and hydrochloric acids (8:2 known as reverse aquaregia) are used for palladium, silver, tin, gold and platinum. Alternative acids can be used if solubility is satisfactory.

For materials that are difficult to digest (e.g. plastics), the addition of 1 mL of hydrogen peroxide to the nitric acid may also be used.

Solutions for mercury require a final matrix containing 1% hydrochloric acid to ensure stability and good washout times in the instrument.

The total inorganic solids must not exceed 0.3% in the final test solution for ICP-MS analysis.

Digested sample solutions should not be considered stable for more than 1 week and dilutions of stock digests should be made on the day of analysis.

8. Instrument Parameters

Startup will optimise the basic performance of the instrument. The optimisation performed in Startup is applied to the basic performance of the instrument. The optimisation specific to the analysis is performed by the auto tune in each batch.

Example of instrument method parameters is detailed below:

| Parameter | Value |
|---|---|
| Acquisition | |
| Number of points per mass | 3 |
| Replicates | 3 |
| Sweep | 100 |
| AutoTune | On |
| P/A factor adjustment | On |
| Peristaltic Pump | |
| Before Acquisition | |
| Uptake Speed | 0.30 rps |
| Uptake Time | 60 sec |
| Stabilisation Time | 60 sec |
| After Acquisition (Probe Rinse) | |
| Rinse Speed | 0.30 rps |
| Rinse on rinse port (sample) | 30 sec |
| Rinse on rinse port (STD) | 30 sec |
| After Acquisition (Rinse) | |
| Rinse Vial 1 | 2 |
| Rinse Speed | 0.30 rps |
| Rinse or rinse vial (Step 1) | 60 sec |
| Rinse or rinse port (Step 1) | 0 sec |
| Rinse Vial 2 | 1 |
| Rinse Speed | 0.30 rps |
| Rinse or rinse vial (Step 2) | 30 sec |
| Rinse or rinse port (Step 2) | 0 sec |
| Rinse Vial 3 | 1 |
| Rinse Speed | 0.20 rps |
| Rinse or rinse vial (Step 3) | 30 sec |
| Rinse or rinse port (Step 3) | 0 sec |
| Execute Pre-emptive rinse | Off |
| Pre-emptive Time | 0 sec |
| Terminate a rinse step at the end of Acq | Off |

9. Analysis

When performing analysis on unknown matrices it is recommended that at least two isotopes of each element are selected (if possible). Data is reported for the isotope based on the following criteria.

Free from polyatomic and isobaric interference
Best QC data
Highest abundance
Perform the following typical injection sequence:

| | ICP-MS |
|---|---|
| Wash | X |
| Cal Blank | X |
| Calibration Standards | X |
| Wash | X |
| IQC standard | X |

-continued

| | ICP-MS |
|---|---|
| Wash | X |
| Samples (including duplicates) | X |
| Spiked sample(s) | X |
| Wash | X |
| Check standard after 10 sample and end of sequence | X |
| Wash | X |

The wash solution is an acid diluent made up to match the acid concentration (or solvent) of the calibration blank. The readings obtained for the wash solutions should be monitored to ensure counts for the elements being tested are returning to their background levels. If this is not the case, the sequence will need to be restarted inserting additional washes as required to ensure minimal carry over between test solutions. Minimal increases in the background readings are allowed.

10. System Suitability—Acceptance Criteria

Reagent/process blank is to be run using the same preparation methods as the sample to assess the background levels of the reagents used for the sample preparation and contamination from external sources. Results may not be reported <3 times the blank concentration.

The RSD of each result reading of analyst and internal standard should be <10%. An RSD above this value indicates poor stability and indication of a possible problem with the instrument, except at levels approaching zero.

The calibration graphs are assessed for linearity. Calibrations should have a correlation coefficient ≥0.998.

A calibration standard should be prepared at the required quantitation/reporting limit if possible. The calculated concentration, based on the calibration must be within 80-120% of the expected concentration (can be skipped if the limit is too high to be included in the analysis, if there is no pre-defined limit, or if the limit is for the collective concentrations of more than one element e.g. total Hg, As and Cd<1 ppm).

A check calibration standard is run every 10 samples, and as the final sample in the sequence, to ensure excessive drift does not occur over the course of the run. The results should be between 85-115% of the expected value.

Results for IQC standards must be within 85-115% of the expected (certified) value.

11. Calculations

Results in ppb: Calculate the concentration of the trace elements using the following equation: Results (ppb)=Concentration in test solution (ppb)×Dilution.

12. Reporting

Trace Element Content: Report the results to 2 significant figures.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. In some embodiments, the term "about" as used herein means +/−2%, 5%, or 10%. In some embodiments, the term "substantially pure" as used herein means 99%, 98%, 95% or 90% pure.

The invention claimed is:

1. A purified composition of a polymer comprising an acetic acid salt of a monomer of formula (I):

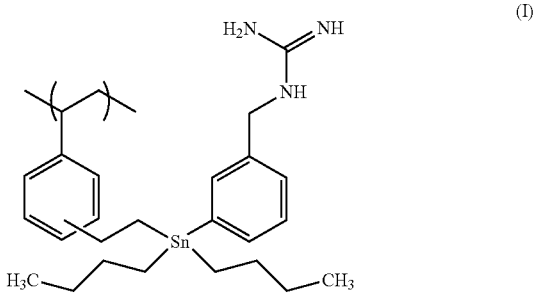

(I)

produced by a method comprising the steps of:
counter ion exchange of a hydrochloric acid form of the monomer of formula (I) with sodium acetate to thereby provide a preparation comprising the monomer of formula (I) in the form of an acetic acid salt;
a first solvent treating step, comprising contacting the preparation with aqueous alcohol, and then removing substantially all of the aqueous alcohol;
a second solvent treating step, comprising contacting the preparation with anhydrous alcohol, and then removing substantially all of the anhydrous alcohol so that a solvent-depleted material comprising the polymer is generated; and
subjecting the solvent-depleted material to vacuum, and to a temperature within a range of about 30° C. to about 50° C., the subjecting being performed under conditions and for a time sufficient to thereby provide the purified composition of the polymer, or pharmaceutically acceptable salt thereof;
wherein no more than 150 ppm of leachable tin is present in the purified composition of the polymer.

2. The composition of claim 1, wherein the aqueous alcohol comprises ethanol.

3. The composition of claim 1, wherein the anhydrous alcohol is or comprises ethanol.

4. The composition of claim 1, wherein the aqueous alcohol is or comprises ethanol and the anhydrous alcohol is or comprises ethanol.

5. The composition of claim 1, the purified composition comprising less than 1.5 wt % water relative to the wt % of the composition.

6. The composition of claim 1, the purified composition comprising less than 1.0 wt % water relative to the wt % of the composition.

7. The composition of claim 1, further comprising a step of:
storing the purified composition under an inert gas.

8. The composition of claim 1, wherein the purified composition comprises less than 2.0 wt % water relative to the wt % of the purified composition.

9. The composition of claim 3, wherein the first solvent treating step comprises treating the preparation with aqueous ethanol.

10. The composition of claim 9, wherein the second solvent treating step comprises treating the preparation with absolute ethanol.

11. The composition of claim 1, wherein the removal of substantially all of the aqueous alcohol or the anhydrous alcohol comprises a first removal step of drying the preparation at ambient temperature and pressure with a flow of nitrogen.

12. The composition of claim 11, wherein the removal of substantially all of the aqueous alcohol or the anhydrous alcohol comprises a first removal step of drying the preparation at ambient temperature and pressure with a flow of nitrogen and then further comprises a second removal step of drying the preparation at ambient temperature under vacuum with a flow of nitrogen.

13. The composition of claim 1, wherein the purified composition comprises not more than about 120 ppm of leachable tin.

14. The composition of claim 1, wherein the purified composition comprises not more than about 90 ppm of leachable tin.

15. The composition of claim 1, wherein the purified composition comprises not more than about 50 ppm of leachable tin.

16. The composition of claim 1, wherein the subjecting is performed under conditions and for a time sufficient so that not more than about 0.5 wt % organic solvent relative to the wt % of the composition is present.

17. The composition of claim 1, wherein the subjecting is performed under conditions and for a time sufficient so that not more than about 0.3 wt % organic solvent relative to the wt % of the composition is present.

* * * * *